(12) United States Patent
Park et al.

(10) Patent No.: US 11,141,098 B2
(45) Date of Patent: Oct. 12, 2021

(54) ELECTRONIC DEVICE FOR MEASURING HYDRATURE USING DISPLAY AND METHOD FOR OPERATING THE SAME

(71) Applicant: Samsung Electronics Co., Ltd., Gyeonggi-do (KR)

(72) Inventors: Sangil Park, Gyeonggi-do (KR); Gitae Mun, Gyeonggi-do (KR); Jinwoo Seo, Seoul (KR); Yongjin Lee, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 330 days.

(21) Appl. No.: 16/159,843

(22) Filed: Oct. 15, 2018

(65) Prior Publication Data

US 2019/0159717 A1 May 30, 2019

(30) Foreign Application Priority Data

Nov. 29, 2017 (KR) ........................ 10-2017-0162071

(51) Int. Cl.
*A61B 5/00* (2006.01)
*H03K 17/96* (2006.01)
(Continued)

(52) U.S. Cl.
CPC ............ *A61B 5/443* (2013.01); *A61B 5/4875* (2013.01); *A61B 5/6898* (2013.01); *A61B 5/742* (2013.01);
(Continued)

(58) Field of Classification Search
CPC ....... H03K 17/962; G06F 3/044; A61B 5/443; A61B 5/6898; A61B 5/4875; A61B 5/7475; A61B 5/742; A61B 2562/0257
See application file for complete search history.

(56) References Cited

U.S. PATENT DOCUMENTS

2005/0119539 A1 6/2005 Bazin
2010/0066693 A1 3/2010 Sato et al.
(Continued)

FOREIGN PATENT DOCUMENTS

EP     1 523 936 B1    11/2009
JP     2009-65390 A    3/2009
(Continued)

OTHER PUBLICATIONS

European Search Report dated Apr. 24, 2019.
Japanese Search Report dated Nov. 5, 2019.

*Primary Examiner* — Devin B Henson
*Assistant Examiner* — Justin Xu
(74) *Attorney, Agent, or Firm* — Cha & Reiter, LLC

(57) ABSTRACT

An electronic device for measuring hydrature, and a method for the same are disclosed. The electronic device includes a display, a capacitive sensor and a processor implementing the method, including setting an attribute of a capacitive sensor using a first value, acquiring a first data measurement from the capacitive sensor in when an external object contacts a display and determining that a touch input has occurred based on the first data, detecting whether the determined touch input satisfies a prespecified condition, setting the operational attribute of the capacitive sensor using a second value when the prespecified condition is satisfied, acquiring a second data measurement from the capacitive sensor while the external object contacts the display when the at least one operational attribute is set using the second value, and determining a hydrature value associated with the external object at least based on the acquired second data measurement.

19 Claims, 14 Drawing Sheets

(51) Int. Cl.
*G06F 3/044* (2006.01)
*H04M 1/72403* (2021.01)

(52) U.S. Cl.
CPC ............ *A61B 5/7475* (2013.01); *G06F 3/044* (2013.01); *H03K 17/962* (2013.01); *A61B 2562/0257* (2013.01)

(56) References Cited

U.S. PATENT DOCUMENTS

| | | |
|---|---|---|
| 2012/0287068 A1 | 11/2012 | Colgate et al. |
| 2013/0157726 A1* | 6/2013 | Miyazaki ............... G06F 1/3231 455/566 |
| 2014/0184536 A1* | 7/2014 | Huang .................... G06F 3/044 345/173 |
| 2015/0009168 A1 | 1/2015 | Levesque et al. |
| 2016/0038037 A1 | 2/2016 | Kovacs |
| 2016/0213316 A1* | 7/2016 | Hyde ..................... A61B 5/4875 |
| 2016/0342276 A1* | 11/2016 | Lu ........................ G09G 3/3659 |
| 2017/0000415 A1 | 1/2017 | Lapetina et al. |
| 2017/0257492 A1* | 9/2017 | Levesque ................ G06F 3/016 |
| 2018/0014787 A1* | 1/2018 | Ganton ................. H03K 17/962 |

FOREIGN PATENT DOCUMENTS

| | | |
|---|---|---|
| JP | 2010-67117 A | 3/2010 |
| JP | 2011-176551 A | 9/2011 |
| JP | 2012-118903 A | 6/2012 |
| JP | 2015-15027 A | 1/2015 |

* cited by examiner

ELECTRONIC DEVICE FOR MEASURING HYDRATURE USING DISPLAY AND METHOD FOR OPERATING THE SAME

CROSS-REFERENCE TO RELATED APPLICATION(S)

This application is based on and claims priority under 35 U.S.C. § 119 to Korean Patent Application No. 10-2017-0162071, filed on Nov. 29, 2017, in the Korean Intellectual Property Office, the disclosure of which is incorporated by reference herein in its entirety.

BACKGROUND

1. Field

This disclosure relates to an electronic device for measuring hydrature using a display and a method for operating the same.

2. Description of Related Art

Various electronic devices such as smart phones, tablet PCs, portable multimedia players (PMPs), personal digital assistants (PDAs), a laptop personal computers and a wearable devices have become popular.

In recent years, interest in skin care and personal grooming is increasing. One of the important factors in skin care is moisturization of skin, because an imbalance in moisture may cause problems such as an over-occurrence of keratin. Accordingly, various techniques for measuring the hydrature of skin (i.e., the hydration of skin) have been developed.

Among the various methods of measuring hydrature of skin, one method for measuring hydrature utilizes an electric signal. Hydrature may be measured by leveraging the fact that the electrical characteristics of an electrical signal applied to skin will change differently depending on the level of hydrature.

SUMMARY

One method for measuring hydrature uses detection of a change in capacitance. The hydrature of a skin is thus measured by a change in electrical characteristics generated between electrodes having a predetermined gap and a dielectric, which is possible when an external object such as a portion of skin touches a display. Further, there may be a separate Corneometer® (e.g., a hand-held device which measures hydrature on contact with skin) that supports the method for measuring hydrature based on capacitance.

However, there is a problem in that a typical hydrature measurement method requires a separate Corneometer® to measure hydrature based on capacitance. It would be beneficial instead to measure hydrature in this way using common electronic devices, such as a smart phone, which is widespread and ubiquitously available to potential users. However, at present, as these specialized electronic devices are required for measuring hydrature, the practice of personal hydrature measurement is not widespread due to the costs of purchasing separate electronic devices such as the Corneometer®.

Objects of the present disclosure are not limited to the above-mentioned objects. That is, other objects that are not mentioned may be obviously understood by those skilled in the art to which the present disclosure pertains from the following description.

Various embodiments of the present disclosure are directed to the provision of an electronic device including: a display including a capacitive sensor, at least one processor configured to set at least one operational attribute of the capacitive sensor using a first value, acquire a first data measurement from the capacitive sensor in when an external object contacts the display while the at least one attribute is set using the first value and determine that a touch input has occurred based on the first data, detect whether the determined touch input satisfies a prespecified condition, and set the at least one operational attribute of the capacitive sensor using a second value when the prespecified condition is satisfied, acquire a second data measurement from the capacitive sensor while the external object contacts the display when the at least one operational attribute is set using the second value, and determine a hydrature value associated with the external object at least based on the acquired second data measurement.

Various embodiments of the present disclosure are directed to the provision of a method for operating an electronic device including: setting at least one operational attribute of a capacitive sensor using a first value, acquiring, by at least one processor, a first data measurement from the capacitive sensor in when an external object contacts a display while the at least one attribute is set using the first value and determine that a touch input has occurred based on the first data, detecting whether the determined touch input satisfies a prespecified condition, and setting the at least one operational attribute of the capacitive sensor using a second value when the prespecified condition is satisfied, acquiring a second data measurement from the capacitive sensor while the external object contacts the display, when the at least one operational attribute is set using the second value, and determining a hydrature value associated with the external object at least based on the acquired second data measurement.

The electronic device for measuring hydrature using a display and the method for operating the same according to various embodiments of the present disclosure can accurately measure hydrature using the change in capacitance occurring when an external object contacts the display.

The electronic device for measuring hydrature using a display and the method for operating the same according to various embodiments of the present disclosure can measure the hydrature using the display supporting the capacitive touch input without the separate external electronic device supporting the measurement of the hydrature.

The electronic device for measuring hydrature using a display and the method for operating the same according to various embodiments of the present disclosure can accurately measure the hydrature using the change in capacitance occurring when an external object contacts the display.

The electronic device for measuring hydrature using a display and the method for operating the same according to various embodiments of the present disclosure can differently set the frequency of the signal input to the capacitive sensor in the touch sensing mode and the hydrature measurement mode, respectively, so that the electronic device may support both of the touch sensing and the hydrature measurement.

The effects that may be achieved by the embodiments of the present disclosure are not limited to the above-mentioned objects. That is, other effects that are not mentioned may be obviously understood by those skilled in the art to which the present disclosure pertains from the following description.

DETAILED DESCRIPTION

Figure 1:
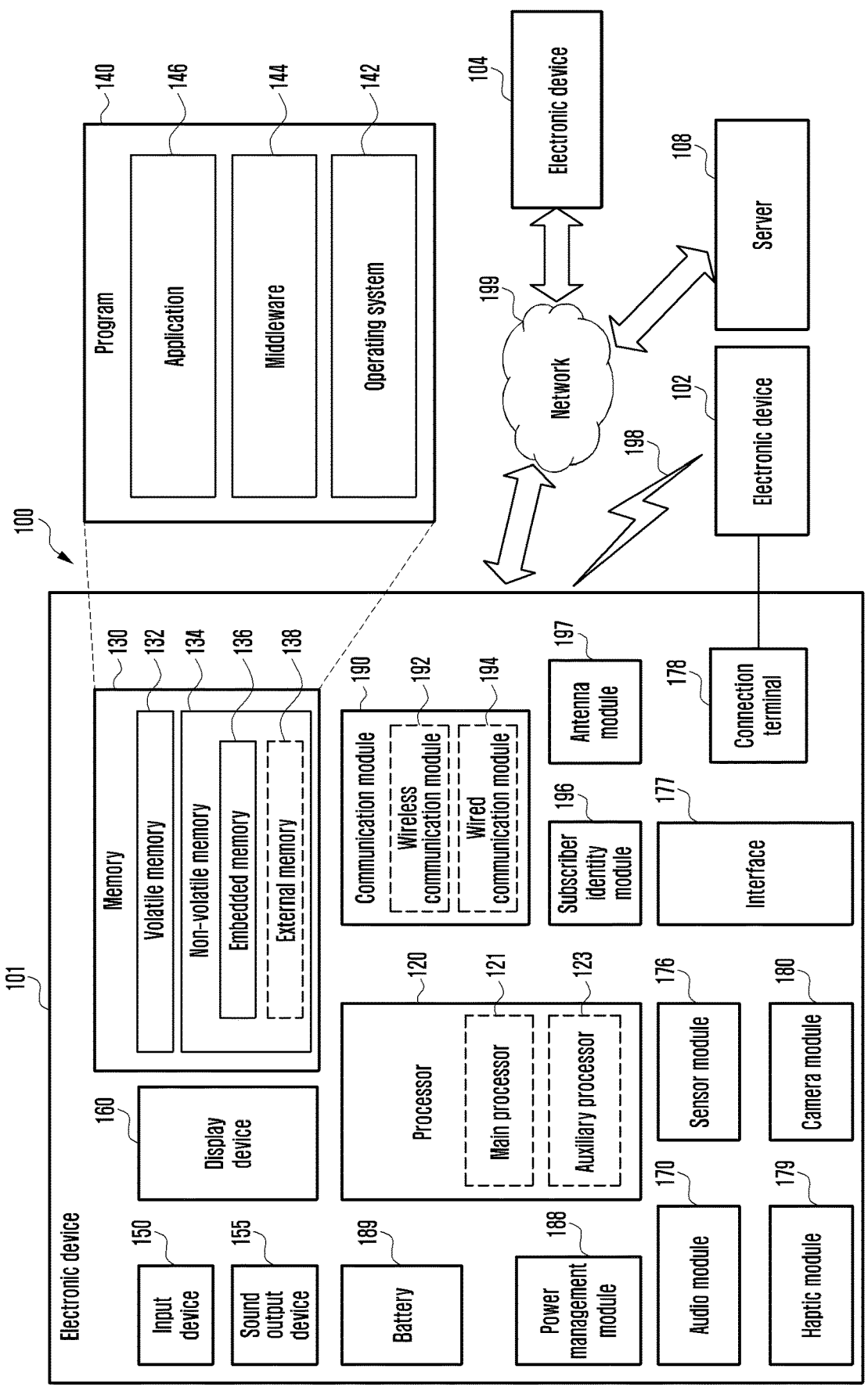
FIG. 1 is a block diagram of an electronic device according to various embodiments of the present disclosure.

FIG. 1 is a block diagram illustrating an electronic device 101 in a network environment 100 according to various embodiments. Referring to FIG. 1, the electronic device 101 in the network environment 100 may communicate with an electronic device 102 via a first network 198 (e.g., a short-range wireless communication network), or an electronic device 104 or a server 108 via a second network 199 (e.g., a long-range wireless communication network). According to an embodiment, the electronic device 101 may communicate with the electronic device 104 via the server 108. According to an embodiment, the electronic device 101 may include a processor 120, memory 130, an input device 150, a sound output device 155, a display device 160, an audio module 170, a sensor module 176, an interface 177, a haptic module 179, a camera module 180, a power management module 188, a battery 189, a communication module 190, a subscriber identification module (SIM) 196, or an antenna module 197. In some embodiments, at least one (e.g., the display device 160 or the camera module 180) of the components may be omitted from the electronic device 101, or one or more other components may be added in the electronic device 101. In some embodiments, some of the components may be implemented as single integrated circuitry. For example, the sensor module 176 (e.g., a fingerprint sensor, an iris sensor, or an illuminance sensor) may be implemented as embedded in the display device 160 (e.g., a display).

The processor 120 may execute, for example, software (e.g., a program 140) to control at least one other component (e.g., a hardware or software component) of the electronic device 101 coupled with the processor 120, and may perform various data processing or computation. According to an embodiment, as at least part of the data processing or computation, the processor 120 may load a command or data received from another component (e.g., the sensor module 176 or the communication module 190) in volatile memory 132, process the command or the data stored in the volatile memory 132, and store resulting data in non-volatile memory 134. According to an embodiment, the processor 120 may include a main processor 121 (e.g., a central processing unit (CPU) or an application processor (AP)), and an auxiliary processor 123 (e.g., a graphics processing unit (GPU), an image signal processor (ISP), a sensor hub processor, or a communication processor (CP)) that is operable independently from, or in conjunction with, the main processor 121. Additionally or alternatively, the auxiliary processor 123 may be adapted to consume less power than the main processor 121, or to be specific to a specified function. The auxiliary processor 123 may be implemented as separate from, or as part of the main processor 121.

The auxiliary processor 123 may control at least some of functions or states related to at least one component (e.g., the display device 160, the sensor module 176, or the communication module 190) among the components of the electronic device 101, instead of the main processor 121 while the main processor 121 is in an inactive (e.g., sleep) state, or together with the main processor 121 while the main processor 121 is in an active state (e.g., executing an application). According to an embodiment, the auxiliary processor 123 (e.g., an image signal processor or a communication processor) may be implemented as part of another component (e.g., the camera module 180 or the communication module 190) functionally related to the auxiliary processor 123.

The memory 130 may store various data used by at least one component (e.g., the processor 120 or the sensor module 176) of the electronic device 101. The various data may include, for example, software (e.g., the program 140) and input data or output data for a command related thererto. The memory 130 may include the volatile memory 132 or the non-volatile memory 134.

The program 140 may be stored in the memory 130 as software, and may include, for example, an operating system (OS) 142, middleware 144, or an application 146.

The input device 150 may receive a command or data to be used by other component (e.g., the processor 120) of the electronic device 101, from the outside (e.g., a user) of the electronic device 101. The input device 150 may include, for example, a microphone, a mouse, or a keyboard.

The sound output device 155 may output sound signals to the outside of the electronic device 101. The sound output device 155 may include, for example, a speaker or a receiver. The speaker may be used for general purposes, such as playing multimedia or playing record, and the receiver may be used for an incoming calls. According to an embodiment, the receiver may be implemented as separate from, or as part of the speaker.

The display device 160 may visually provide information to the outside (e.g., a user) of the electronic device 101. The display device 160 may include, for example, a display, a hologram device, or a projector and control circuitry to control a corresponding one of the display, hologram device, and projector. According to an embodiment, the display device 160 may include touch circuitry adapted to detect a touch, or sensor circuitry (e.g., a pressure sensor) adapted to measure the intensity of force incurred by the touch.

The audio module 170 may convert a sound into an electrical signal and vice versa. According to an embodiment, the audio module 170 may obtain the sound via the input device 150, or output the sound via the sound output device 155 or a headphone of an external electronic device (e.g., an electronic device 102) directly (e.g., wiredly) or wirelessly coupled with the electronic device 101.

The sensor module 176 may detect an operational state (e.g., power or temperature) of the electronic device 101 or an environmental state (e.g., a state of a user) external to the electronic device 101, and then generate an electrical signal or data value corresponding to the detected state. According to an embodiment, the sensor module 176 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 177 may support one or more specified protocols to be used for the electronic device 101 to be coupled with the external electronic device (e.g., the electronic device 102) directly (e.g., wiredly) or wirelessly. According to an embodiment, the interface 177 may include, for example, a high definition multimedia interface (HDMI), a universal serial bus (USB) interface, a secure digital (SD) card interface, or an audio interface.

A connecting terminal 178 may include a connector via which the electronic device 101 may be physically connected with the external electronic device (e.g., the electronic device 102). According to an embodiment, the connecting terminal 178 may include, for example, a HDMI connector, a USB connector, a SD card connector, or an audio connector (e.g., a headphone connector).

The haptic module 179 may convert an electrical signal into a mechanical stimulus (e.g., a vibration or a movement) or electrical stimulus which may be recognized by a user via his tactile sensation or kinesthetic sensation. According to an embodiment, the haptic module 179 may include, for example, a motor, a piezoelectric element, or an electric stimulator.

The camera module 180 may capture a still image or moving images. According to an embodiment, the camera module 180 may include one or more lenses, image sensors, image signal processors, or flashes.

The power management module 188 may manage power supplied to the electronic device 101. According to an embodiment, the power management module 188 may be implemented as at least part of, for example, a power management integrated circuit (PMIC).

The battery 189 may supply power to at least one component of the electronic device 101. According to an embodiment, the battery 189 may include, for example, a primary cell which is not rechargeable, a secondary cell which is rechargeable, or a fuel cell.

The communication module 190 may support establishing a direct (e.g., wired) communication channel or a wireless communication channel between the electronic device 101 and the external electronic device (e.g., the electronic device 102, the electronic device 104, or the server 108) and performing communication via the established communication channel. The communication module 190 may include one or more communication processors that are operable independently from the processor 120 (e.g., the application processor (AP)) and supports a direct (e.g., wired) communication or a wireless communication. According to an embodiment, the communication module 190 may include a wireless communication module 192 (e.g., a cellular communication module, a short-range wireless communication module, or a global navigation satellite system (GNSS) communication module) or a wired communication module 194 (e.g., a local area network (LAN) communication module or a power line communication (PLC) module). A corresponding one of these communication modules may communicate with the external electronic device via the first network 198 (e.g., a short-range communication network, such as Bluetooth™, wireless-fidelity (Wi-Fi) direct, or infrared data association (IrDA)) or the second network 199 (e.g., a long-range communication network, such as a cellular network, the Internet, or a computer network (e.g., LAN or wide area network (WAN)). These various types of communication modules may be implemented as a single component (e.g., a single chip), or may be implemented as multi components (e.g., multi chips) separate from each other. The wireless communication module 192 may identify and authenticate the electronic device 101 in a communication network, such as the first network 198 or the second network 199, using subscriber information (e.g., international mobile subscriber identity (IMSI)) stored in the subscriber identification module 196.

The antenna module 197 may transmit or receive a signal or power to or from the outside (e.g., the external electronic device) of the electronic device 101. According to an embodiment, the antenna module 197 may include one or more antennas, and, therefrom, at least one antenna appropriate for a communication scheme used in the communication network, such as the first network 198 or the second network 199, may be selected, for example, by the communication module 190 (e.g., the wireless communication module 192). The signal or the power may then be transmitted or received between the communication module 190 and the external electronic device via the selected at least one antenna.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, commands or data may be transmitted or received between the electronic device 101 and the external electronic device 104 via the server 108 coupled with the second network 199. Each of the electronic devices 102 and 104 may be a device of a same type as, or a different type, from the electronic device 101. According to an embodiment, all or some of operations to be executed at the electronic device 101 may be executed at one or more of the external electronic devices 102, 104, or 108. For example, if the electronic device 101 should perform a function or a service automatically, or in response to a request from a user or another device, the electronic device 101, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 101. The electronic device 101 may provide the outcome, with or without further processing of the outcome, as at least part of a reply to the request. To that end, a cloud computing, distributed computing, or client-server computing technology may be used, for example.

The electronic device according to various embodiments may be one of various types of electronic devices. The electronic devices may include, for example, a portable communication device (e.g., a smart phone), a computer device, a portable multimedia device, a portable medical device, a camera, a wearable device, or a home appliance. According to an embodiment of the disclosure, the electronic devices are not limited to those described above.

It should be appreciated that various embodiments of the present disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. It is to be understood that a singular form of a noun corresponding to an item may include one or more of the things, unless the relevant context clearly indicates otherwise. As used herein, each of such phrases as "A or B," "at least one of A and B," "at least one of A or B," "A, B, or C," "at least one of A, B, and C," and "at least one of A, B, or C," may include all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with," "coupled to," "connected with," or "connected to" another element (e.g., a second element), it means that the element may be coupled with the other element directly (e.g., wiredly), wirelessly, or via a third element.

As used herein, the term "module" may include a unit implemented in hardware, software, or firmware, and may interchangeably be used with other terms, for example, "logic," "logic block," "part," or "circuitry". A module may be a single integral component, or a minimum unit or part thereof, adapted to perform one or more functions. For example, according to an embodiment, the module may be implemented in a form of an application-specific integrated circuit (ASIC).

Various embodiments as set forth herein may be implemented as software (e.g., the program 140) including one or more instructions that are stored in a storage medium (e.g., internal memory 136 or external memory 138) that is readable by a machine (e.g., the electronic device 101). For example, a processor (e.g., the processor 120) of the machine (e.g., the electronic device 101) may invoke at least one of the one or more instructions stored in the storage medium, and execute it, with or without using one or more other components under the control of the processor. This allows the machine to be operated to perform at least one function according to the at least one instruction invoked. The one or more instructions may include a code generated or executed by a compiler or a code executable by an interpreter. The machine-readable storage medium may be provided in the form of a non-transitory storage medium. Further, the term "non-transitory" simply means that the storage medium is a tangible device, and does not include a signal (e.g., an electromagnetic wave), but this term does not differentiate between where data is semi-permanently stored in the storage medium and where the data is temporarily stored in the storage medium.

According to an embodiment, a method according to various embodiments of the disclosure may be included and provided in a computer program product. The computer program product may be traded as a product between a seller and a buyer. The computer program product may be distributed in the form of a machine-readable storage medium (e.g., compact disc read only memory (CD-ROM)), or be distributed (e.g., downloaded or uploaded) online via an application store (e.g., Play Store™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to various embodiments, each component (e.g., a module or a program) of the above-described components may include a single entity or multiple entities. According to various embodiments, one or more of the above-described components may be omitted, or one or more other components may be added. Alternatively or additionally, a plurality of components (e.g., modules or programs) may be integrated into a single component. In such a case, according to various embodiments, the integrated component may still perform one or more functions of each of the plurality of components in the same or similar manner as they are performed by a corresponding one of the plurality of components before the integration. According to various embodiments, operations performed by the module, the program, or another component may be carried out sequentially, in parallel, repeatedly, or heuristically, or one or more of the operations may be executed in a different order or omitted, or one or more other operations may be added.

Figure 2:
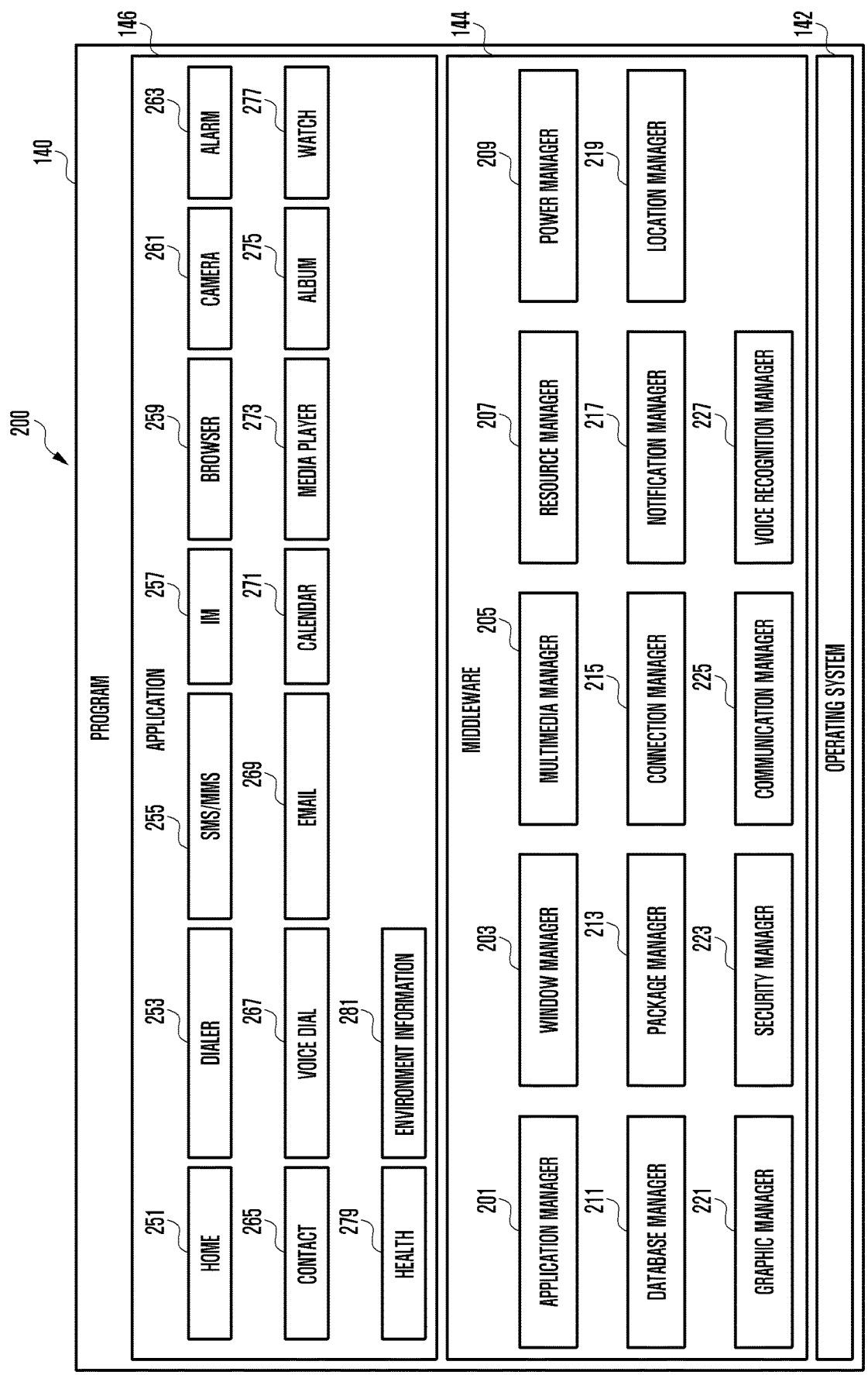
FIG. 2 is a block diagram of a program according to various embodiments of the present disclosure.

FIG. 2 is a block diagram 200 illustrating the program 140 according to various embodiments. According to an embodiment, the program 140 may include an operating system (OS) 142 to control one or more resources of the electronic device 101, middleware 144, or an application 146 executable in the OS 142. The OS 142 may include, for example, Android™, iOS™, Windows™, Symbian™, Tizen™, or Bada™. At least part of the program 140, for example, may be pre-loaded on the electronic device 101 during manufacture, or may be downloaded from or updated by an external electronic device (e.g., the electronic device 102 or 104, or the server 108) during use by a user.

The OS 142 may control management (e.g., allocating or deallocation) of one or more system resources (e.g., process, memory, or power source) of the electronic device 101. The OS 142, additionally or alternatively, may include one or more driver programs to drive other hardware devices of the electronic device 101, for example, the input device 150, the sound output device 155, the display device 160, the audio module 170, the sensor module 176, the interface 177, the haptic module 179, the camera module 180, the power management module 188, the battery 189, the communication module 190, the subscriber identification module 196, or the antenna module 197.

The middleware 144 may provide various functions to the application 146 such that a function or information provided from one or more resources of the electronic device 101 may be used by the application 146. The middleware 144 may include, for example, an application manager 201, a window manager 203, a multimedia manager 205, a resource manager 207, a power manager 209, a database manager 211, a package manager 213, a connectivity manager 215, a notification manager 217, a location manager 219, a graphic manager 221, a security manager 223, a telephony or call manager 225, or a voice recognition manager 227.

The application manager 201, for example, may manage the life cycle of the application 146. The window manager 203, for example, may manage one or more graphical user interface (GUI) resources that are used on a screen. The multimedia manager 205, for example, may identify one or more formats to be used to play media files, and may encode or decode a corresponding one of the media files using a codec appropriate for a corresponding format selected from the one or more formats. The resource manager 207, for example, may manage the source code of the application 146 or a memory space of the memory 130. The power manager 209, for example, may manage the capacity, temperature, or power of the battery 189, and determine or provide related information to be used for the operation of the electronic device 101 based at least in part on corresponding information of the capacity, temperature, or power of the battery 189. According to an embodiment, the power manager 209 may interwork with a basic input/output system (BIOS) (not shown) of the electronic device 101.

The database manager 211, for example, may generate, search, or change a database to be used by the application 146. The package manager 213, for example, may manage installation or update of an application that is distributed in the form of a package file. The connectivity manager 215, for example, may manage a wireless connection or a direct connection between the electronic device 101 and the external electronic device. The notification manager 217, for example, may provide a function to notify a user of an occurrence of a specified event (e.g., an incoming call, message, or alert). The location manager 219, for example, may manage locational information on the electronic device 101. The graphic manager 221, for example, may manage one or more graphic effects to be offered to a user or a user interface related to the one or more graphic effects.

The security manager 223, for example, may provide system security or user authentication. The telephony manager 225, for example, may manage a voice call function or a video call function provided by the electronic device 101. The voice recognition manager 227, for example, may transmit a user's voice data to the server 108, and receive, from the server 108, a command corresponding to a function to be executed on the electronic device 101 based at least in part on the voice data, or text data converted based at least in part on the voice data. According to an embodiment, the middleware 244 may dynamically delete some existing components or add new components. According to an embodiment, at least part of the middleware 144 may be included as part of the OS 142 or may be implemented as another software separate from the OS 142.

The application 146 may include, for example, a home 251, dialer 253, short message service (SMS)/multimedia messaging service (MMS) 255, instant message (IM) 257, browser 259, camera 261, alarm 263, contact 265, voice recognition 267, email 269, calendar 271, media player 273, album 275, watch 277, health 279 (e.g., for measuring the degree of workout or biometric information, such as blood sugar), or environment information 281 (e.g., for measuring air pressure, humidity, or temperature information) application. According to an embodiment, the application 146 may further include an information exchanging application (not shown) that is capable of supporting information exchange between the electronic device 101 and the external electronic device. The information exchange application, for example, may include a notification relay application adapted to transfer designated information (e.g., a call, message, or alert) to the external electronic device or a device management application adapted to manage the external electronic device. The notification relay application may transfer notification information corresponding to an occurrence of a specified event (e.g., receipt of an email) at another application (e.g., the email application 269) of the electronic device 101 to the external electronic device. Additionally or alternatively, the notification relay application may receive notification information from the external electronic device and provide the notification information to a user of the electronic device 101.

The device management application may control the power (e.g., turn-on or turn-off) or the function (e.g., adjustment of brightness, resolution, or focus) of the external electronic device or some component thereof (e.g., a display device or a camera module of the external electronic device). The device management application, additionally or alternatively, may support installation, delete, or update of an application running on the external electronic device.

Figure 3:
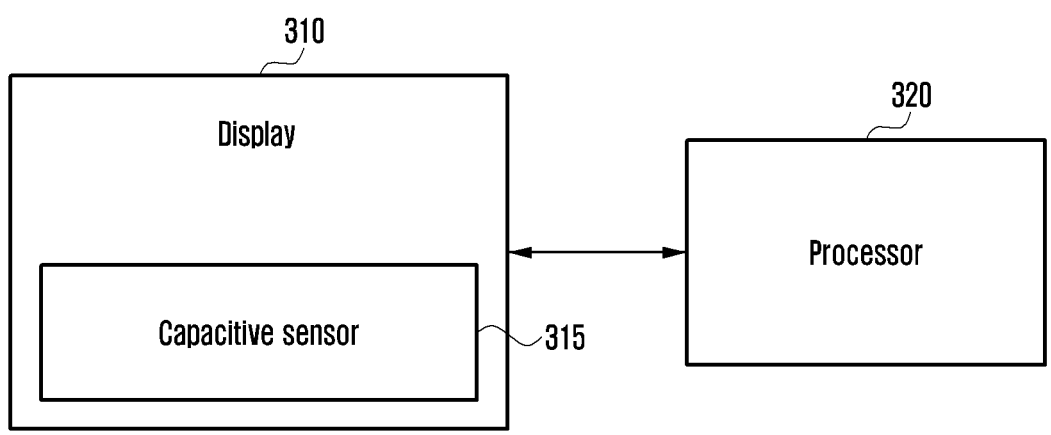
FIG. 3 is a block diagram of an electronic device according to various embodiments of the present disclosure.

FIG. 3 is a block diagram of an electronic device according to various embodiments of the present disclosure.

Referring to FIG. 3, an electronic device (e.g., an electronic device 101 in FIG. 1) according to various embodiments of the present disclosure includes a display (e.g., display devices 160 in FIG. 1, 310) and a processor (e.g., processor(s) 120 in FIG. 1, 320 in FIG. 3).

The display 310 may display various image videos according to the control of the processor 320.

According to various embodiments of the present disclosure, the display 310 may be implemented in the form of a touch sensor panel (TSP) that can recognize contact or proximity (e.g., hovering) of various external objects. The touch sensor panel may be implemented in various structures (G2, G1F, GFF, GFd, GF2, GF1, GF, and the like) and types, and it should be understood that the implementations and contents of the present disclosure may be applied independent of the structure and the type of the touch sensor panel.

The display 310 may include a capacitive sensor 315 to recognize contact or proximity of various external objects. The capacitive sensor 315 may include a plurality of capacitors, and the capacitive sensor 315 may apply an electric signal to the capacitors. The capacitor may charge and discharge electric charges corresponding to the application of the electric signal. When the electric signal is applied to the capacitor, the capacitor may be charged with electric charges according to a magnitude in voltage of the electric signal. The display 310 may receive a touch input based on the signal collected by the capacitive sensor 315.

According to various embodiments of the present disclosure, the capacitive sensor 315 may apply an electrical signal having a set cycle to each of the capacitors included in the capacitive sensor 315. The capacitors included in the capacitive sensor 315 may repeatedly charge and discharge electric charges according to the cycle of the electric signal. A frequency of the electrical signal having a reciprocal relationship of the cycle of the electrical signal may be associated with a scan frequency which is used to detect a change amount in a charge amount of the capacitive sensor 315 or a charge amount of the capacitive sensor 315.

The charging and discharging of the capacitor included in the capacitive sensor 315 will be described with reference to FIG. 4A.

According to various embodiments of the present disclosure, when the external object contacts or proximate to the display 310, the electric charges charged in the capacitor may be discharged by a capacitance component of the external object. The capacitive sensor 315 may determine whether the external object contacts or proximate to the display 310 based on a physical amount that is changed due to the capacitance component of the external object. For example, the capacitive sensor 315 may determine whether the external object contacts or proximate the display 310 based on the change in capacitance of the capacitive sensor 315 or the change amount in the charge amount. Another example, the capacitive sensor 315 may confirm the charge amount of the capacitive sensor 315 and determine whether the external object contacts or proximate to the display 310 based on a comparison value of the charge amount with a threshold.

According to various embodiments of the present disclosure, the capacitive sensor 315 may be implemented using various methods such as self capacitance and mutual capacitance, and the contents of the present disclosure may be applied independent of the scheme of using the capacitive sensor 315.

The processor 320 may perform a control on the capacitive sensor 315 and measure hydrature for at least a part of the external object contacting the display 310.

According to various embodiments of the present disclosure, the processor 320 may set at least one attribute associated with the capacitive sensor 315 as a first attribute.

At least one attribute associated with the capacitive sensor 315 may mean information associated with charging/discharging cycle of the capacitive sensor 315, a charge amount value that the capacitive sensor 315 can charge, and various physical amounts (voltage, current, capacitance, etc.) that the capacitive sensor 31 can measure. The processor 320 may control the capacitive sensor 315 to operate the capacitive sensor 315 in a state in which the at least one attribute is set as the first attribute.

According to various embodiments of the present disclosure, the operation of the capacitive sensor 315 based on a first attribute may mean the operation for sensing a contact or proximate of various external objects to the display 310.

The processor 320 may acquire first data associated with a physical amount (a change in capacitance or a change in a charge amount, a charge amount) of the capacitive sensor 315 in a state in which the capacitive sensor 315 is operated with the first attribute. According to various embodiments of the present disclosure, the first data may include a change amount in physical amount measured by the capacitive sensor 315.

The processor 320 may confirm the first data and determine a touch input to the display 310 based on at least the first data.

According to various embodiments of the present disclosure, the content displayed on the display 310 may include guide information indicating a location at which an external object contacts the display 310, guide information indicating a time when an external object keeps contacting the display 310, guide information indicating a minimum contact area generated while the external object contacts the display 310, and the like.

According to various embodiments of the present disclosure, the touch input to the display 310 may be determined based on the first data which includes the change in physical amount (a change in a charge amount or a change in capacitance of the capacitive sensor 315) of the capacitive sensor 315 which is generated while the external object contacts or proximate the display 310.

According to various embodiments of the present disclosure, the content displayed on the display 310 may refer to various screens. For example, graphic objects such as a virtual keypad and a button for performing a user input may be displayed on the display 310. According to various embodiments of the present disclosure, the processor 320 may determine the touch input (e.g., a type of key input on the virtual keypad, a touch of the button, etc.) to the display 310 based on the first data.

The processor 320 may set at least one attribute associated with the capacitive sensor 315 as a second attribute if the specified condition is satisfied. According to various embodiments of the present disclosure, the processor 320 may set at least one attribute associated with the capacitive sensor 315 as the second attribute in order to measure hydrature of an external object.

According to various embodiments of the present disclosure, the specified condition may include various conditions which may be determined to measure the hydrature of the external object. Various conditions such as a location and a size of a region in which the external object contacts the display 310, a pressure applied to the display 310 while the external object contacts the display 310, and a time when the external object keeps contacting the display 310 may refer to various conditions that can be determined to measure the hydrature of the external object. For example, if the area of the region in which the external object contacts the display 310 is greater than or equal to (or exceeds) a set value or the time when the external object keeps contacting the display 310 is greater than or equal to (or exceeds) the set value, the processor 320 may determine that the specified condition is satisfied. According to various embodiments of the present disclosure, the processor 320 may determine whether the contact of the external object according to the guide information displayed on the display 310 satisfies the specified condition. According to various embodiments of the present disclosure, the guide information displayed on the display 310 may include guide information indicating a location at which an external object contacts the display 310, guide information indicating a time when an external object keeps contacting the display 310, guide information indicating a minimum contact area generated while the external object contacts the display 310, and the like.

According to various embodiments of the present disclosure, the processor 320 may perform the operations associated with the measurement of the hydrature when the physical amount (e.g., the size of the contact area of the external object with the display 310, the contact holding time, etc.) generated by the contact of the external object satisfies the specified condition, regardless of the user intention of the electronic device 300. For example, when a portion (e.g., user's ear) of a user's body contacts or proximate the electronic device 300 (e.g., a situation in which the electronic device 300 performs a call), the processor 320 may set at least one attribute of the capacitive sensor 315 as the second attribute based on the first data including the size of the contact area generated while a part of the user's body contacts the display 310, the contact holding time, etc.

According to various embodiments of the present disclosure, at least one attribute associated with the capacitive sensor 315 may mean information associated with charging/discharging cycle of the capacitive sensor 315, a charge amount value that the capacitive sensor 315 can charge, and various physical amounts (voltage, current, capacitance, etc.) that the capacitive sensor 31 can measure.

According to various embodiments of the present disclosure, the processor 320 may change at least one attribute associated with the capacitive sensor 315 from the first attribute to the second attribute, in response to the determination that the specified condition is satisfied. The processor 320 may acquire second data associated with the change in capacitance or the change in a charge amount of the capacitive sensor 315 or the charge amount while the capacitive sensor 315 is operated as the second attribute. The second data may be used to determine the hydrature associated with the external object contacting the display 310.

According to various embodiments of the present disclosure, the processor 320 may change the frequency of the signal input to the capacitive sensor 315 from a frequency corresponding to the first attribute to a frequency corresponding to the second attribute. By changing the frequency of the signal input to the capacitive sensor 315 to the frequency corresponding to the second attribute, the processor 320 may change a charge/discharge rate of the capacitive sensor 315.

According to various embodiments of the present disclosure, the operation of setting, by the processor 320, at least one attribute of the capacitive sensor 315 as the second attribute may mean blocking the signal input for charging the capacitive sensor 315.

When the signal input to the capacitive sensor 315 for charging is blocked, the charging of electric charge in the capacitive sensor 315 may stop. The processor 320 may block the signal input to charge the capacitive sensor 315 in order to confirm the change amount in the charge amount of the capacitive sensor 315 occurring due to the contact of the external object or the charge amount changed due to the contact of the external object (see FIG. 4B).

To accurately measure the hydrature of the external object, it is possible to stop charging the electric charge of the capacitive sensor 315 and measure the hydrature of the external object based on the charge amount remaining in the capacitive sensor 315.

According to various embodiments of the present disclosure, the operation of setting, by the processor 320, at least one attribute of the capacitive sensor 315 as a second attribute may mean that the signal having lower frequency than the frequency corresponding to the first attribute is input to the capacitive sensor 315.

When the frequency of the signal input to charge the capacitive sensor 315 is lowered, the charging/discharging rate of the capacitive sensor 315 can be lowered and the charge amount charged in the capacitive sensor 315 may be reduced. In order to more accurately confirm the change amount in the charge amount of the capacitive sensor 315 due to the contact of the external object, the processor 320 may set the frequency of the signal input to charge the capacitive sensor 315 to be lower than the frequency correspond to the first attribute (see FIG. 4C).

According to various embodiments of the present disclosure, the processor 320 may increase the charge/discharge rate of the capacitive sensor 315 so that the capacitive sensor 315 is charged with a charge amount greater than or equal to (or exceeding) the set charge amount. The processor 320 may set at least one attribute of the capacitive sensor 315 as the second attribute when the charge amount of the capacitive sensor 315 is greater than or equal to (or exceeds) the set charge amount.

The operation of the capacitive sensor 315 based on the first attribute may mean the operation for sensing a touch input by various external objects on the display 310, and the operation of the capacitive sensor 315 based on the second attribute may mean the operation for determining the hydrature of the external object contacting the display 310.

According to various embodiments of the present disclosure, the processor 320 may control the charge amount of the capacitive sensor 315 corresponding to the first attribute to be smaller than that of the capacitive sensor 315 corresponding to the second attribute. It may be possible to detect the touch input on the display 310 even if the change amount in the charge amount of the capacitive sensor 315 is not large. This is because, in order to measure the hydrature of the external object, the resolution of the hydrature measurement may increase as the charge amount of the capacitive sensor 315 increases. Therefore, the processor 320 may control the charge amount of the capacitive sensor 315 corresponding to the first attribute to be smaller than that of the capacitive sensor 315 corresponding to the second attribute.

According to various embodiments of the present disclosure, the processor 320 may determine the hydrature associated with the external object that contacts the display 310 based on at least a part of the second data.

According to various embodiments of the present disclosure, the electronic device 101 may further includes a memory (e.g., a memory 130 in FIG. 1) that temporarily or non-temporally stores a table to which the change amount in the charge amount of the capacitive sensor 315 and the hydrature are mapped.

According to various embodiments of the present disclosure, the processor 320 may confirm the change amount in the charge amount of the capacitive sensor 315 or the charge amount changed due to the contact of the external object in the second data. The processor 320 may confirm the hydrature mapped to the charge amount confirmed in the table.

According to various embodiments of the present disclosure, the change amount in the charge amount and the hydrature may have a correlation that the change amount in the charge amount increases as the hydrature of the external object increases. The table stored in the memory 130 may mean a table including data on the correlation described above. The table will be described later with reference to FIG. 6.

According to various embodiments of the present disclosure, the processor 320 may detect various situations (e.g., a situation in which a user uses the electronic device 101 to perform a call, a situation in which a part of a user's body contacts the display 310, etc. while a user holds the electronic device 101) in which a portion (e.g., a user's ear, a part of a user's face, a part of a user's hand, etc.) of a user's body contacts the display 310 and may perform the hydrature measurement on a part of the user's body.

For example, the processor 320 may confirm whether the electronic device 101 is operating in a call mode. According to various embodiments of the present disclosure, the call mode may mean an operation mode in which the electronic device 101 uses a communication module (e.g., a communication module 190 in FIG. 1) to transmit and receive voice data and the like to and from an external electronic device.

According to various embodiments of the present disclosure, the processor 320 may confirm data that the communication module 190 transmits to confirm whether the electronic device 101 is operating in the call mode.

According to various embodiments of the present disclosure, the processor 320 may use a sensor module (e.g., a sensor module 176 in FIG. 1) that includes a grip sensor, a proximity sensor using infrared light, or the like to confirm whether the electronic device 101 is operating in the call mode. For example, the processor 320 may use data indicating whether the user output by the grip sensor holds the portable terminal (i.e., electronic device) 101, data indicating whether a part of the user's body proximate the portable terminal (i.e., electronic device) 101, or the like to confirm whether the electronic device 101 is operating in the call mode.

According to various embodiments of the present disclosure, the processor 320 may set at least one attribute of the capacitive sensor 315 as the second attribute in response to confirming that the electronic device 101 enters the call mode. The processor 320 may measure the hydrature on a part of the user's body that contacts the display 310 while the capacitive sensor 315 is operating based on the second attribute. Using the above method, the processor 320 may measure the hydrature on a part of a user's body while the user makes a call.

According to various embodiments of the present disclosure, the processor 320 may provide various application services using the measured hydrature.

For example, the processor 320 may enable an access authorized application to use the measured hydrature. For example, the processor 320 may grant an access of an application providing hydrature information to the measured hydrature information. The processor 320 may output the measured hydrature and various additional information associated with the measured hydrature on the display 310.

As another example, the processor 320 may transmit the measured hydrature to external devices (e.g., a server, etc.) using the communication module 190. The external device may use the received hydrature information to generate various information (a list of products associated with the measured hydrature, a result of a skin age of a user using the measured hydrature, information associated with an oil/water balance using the measured hydrature, proposal for water ingestion, etc.) associated with a user's skin and transmit the generated information to the electronic device 101.

Figure 4A:
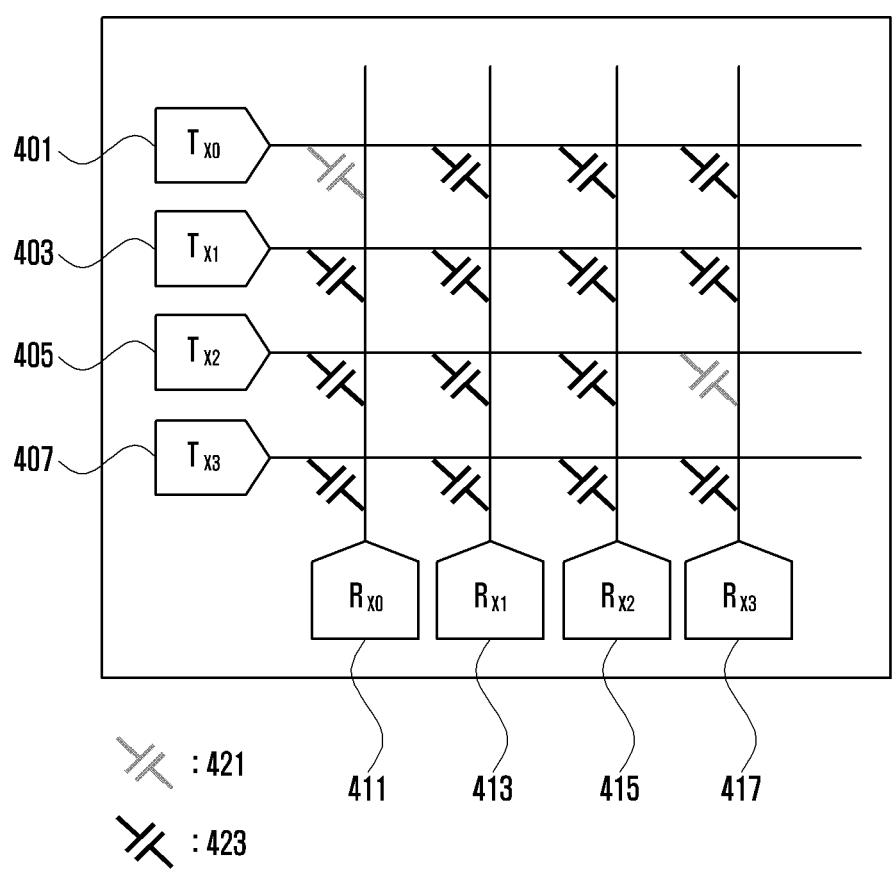
FIG. 4A is a diagram illustrating a capacitive sensor in an electronic device according to various embodiments of the present disclosure.

FIG. 4A is a diagram illustrating a capacitive sensor in an electronic device according to various embodiments of the present disclosure.

Referring to FIG. 4A, the capacitive sensor (e.g., the capacitive sensor 315 in FIG. 3) included in an electronic device (e.g., 100) according to various embodiments of the present disclosure includes a plurality of transmit channels (Tx channels) 401, 403, 405, and 407, a plurality of receive channels (Rx channels) 411, 413, 415, and 417, and capacitors 421 and 423 connected to each of a plurality of transmit channels and a plurality of receive channels.

According to various embodiments of the present disclosure, the capacitive sensor 315 may include capacitors connected between each of the plurality of transmit channels and each of the plurality of receive channels. Each of the capacitors may change the charge amount charged in the capacitor due to the contact of the external object. Referring to FIG. 4A, there are shown capacitors 421 whose charge amount is changed due to the contact of the external object and capacitors 423 whose charge amount is maintained without the contact with the external object.

According to various embodiments of the present disclosure, the capacitive sensor 315 may generate a signal having a frequency for detecting a change in capacitance, under the control of the processor (e.g., the processor 320 in FIG. 3). For example, the capacitive sensor 315 may transmit an electrical signal for charging electric charges of the capacitors 421 and 423 to the transmit channels 401, 403, 405, and 407, and the capacitors 421 and 423 may receive an electrical signal from the transmit channels 401, 403, 405, and 407 to charge electric charges. The capacitive sensor 315 may measure the charge amount in each of the capacitors 421 and 423 using the electrical signal received from the receive channels 411, 413, 415, and 417. According to various embodiments of the present disclosure, the capacitors (e.g., 421) may charge electric charges using a voltage or a current that the transmit channel (e.g., 403) transmits, and the capacitors (e.g., 421) may discharge electric charges based on a voltage or a current that the transmit channel (e.g., 403) transmits.

According to various embodiments of the present disclosure, the capacitive sensor 315 may detect whether the external object contacts the display 310 based on the change in the charge amount of the capacitors 421 and 423 or the change in capacitance which is generated while the external object contacts the display (e.g., the display 310 in FIG. 3) or the charge amount of the capacitors 421 and 423.

According to various embodiments of the present disclosure, the processor 320 may determine the hydrature of the external object based on the change amount in the charge amount of the capacitors 421 and 423 or the change amount in capacitance which is generated while the external object contacts the display 310 or the charge amount of the capacitors 421 and 423. For example, the change amount in charge amount may vary depending on the hydrature of the external object. The higher the hydrature of the external object, the higher the electrical conductivity of the external object, and the electric charges stored in the capacitors 421 and 423 may more exit to the external object. Conversely, the lower the hydrature of the external object, the lower the electrical conductivity of the external object, and the electric charges stored in the capacitors 421 and 423 may less exit to the external object. Using this principle, the processor 320 may determine the hydrature of the external object based on the change amount in the charge amount.

According to various embodiments of the present disclosure, the processor 320 may confirm the charge amount remaining in the capacitors 421 and 423 based on the signal transmitted from the receive channels 411, 413, 415, and 417, and determine the hydrature of the external object based on the remaining charge amount.

According to various embodiments of the present disclosure, the processor 320 may set at least one attribute (charging/discharging cycle of the capacitive sensor 315, charging/discharging frequency of the capacitive sensor 315, charging capacity of the capacitive sensor 315 etc.) associated with the capacitive sensor as the first attribute in order to detect whether the external object touches the display 310.

According to various embodiments of the present disclosure, the processor 320 may determine at least one attribute associated with the capacitive sensor 315 as the second attribute in order to determine the hydrature of the external object.

According to various embodiments of the present disclosure, the first attribute and the second attribute may mean an attribute of a frequency of a signal output from the transmit channel 401, 403, 405, or 407 of the capacitive sensor 315. This will be described later with reference to FIGS. 4B and 4E.

FIGS. 4B to 4E are diagrams illustrating a signal input from the transmit channel to the receive channel of the capacitive sensor in the electronic device according to various embodiments of the present disclosure.

Figure 4B:
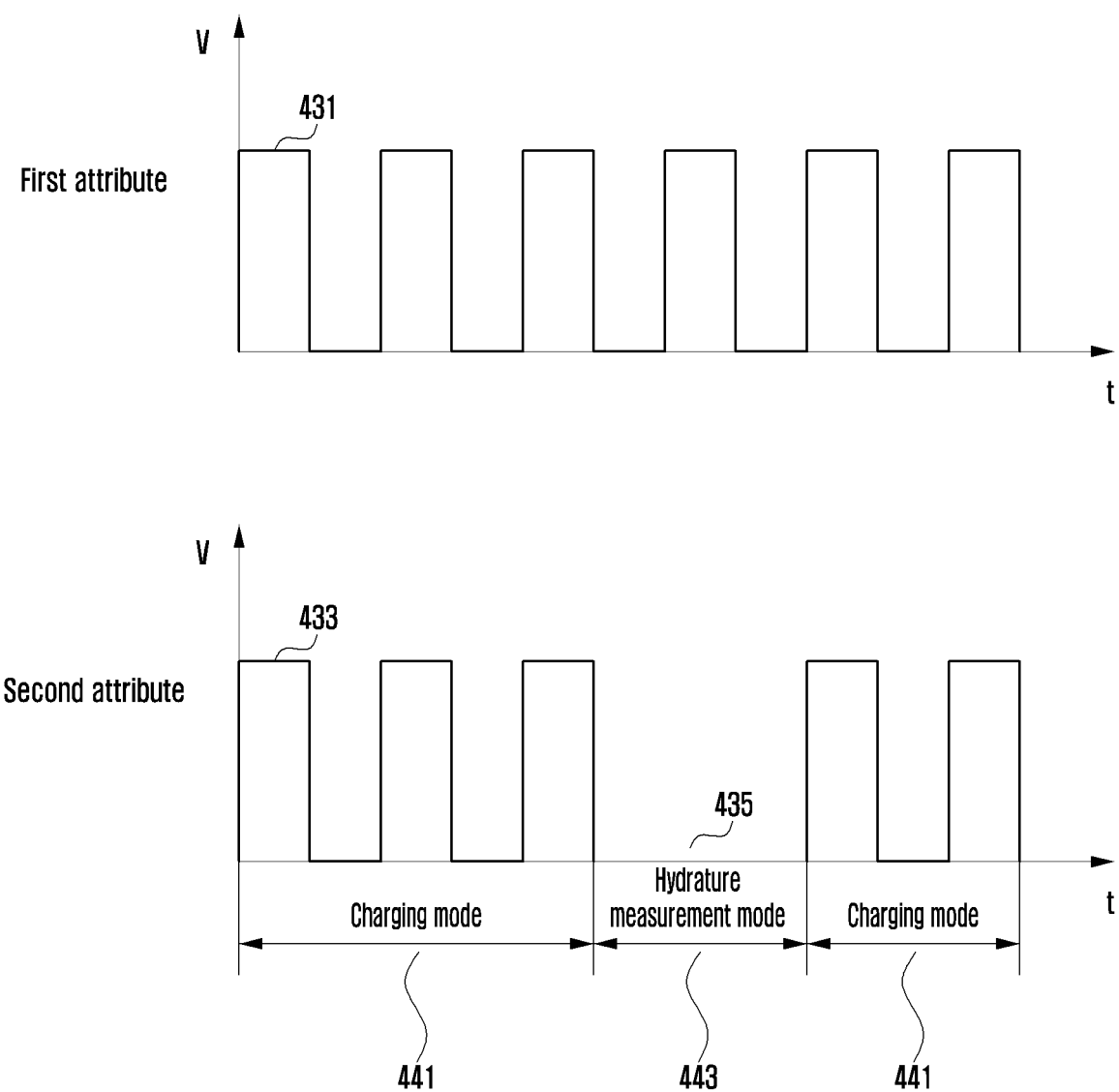
FIG. 4B, FIG. 4C, FIG. 4D and FIG. 4E are diagrams illustrating a signal input to the capacitive sensor in the electronic device according to various embodiments of the present disclosure.

Referring to FIG. 4B, a signal 431 transmitted from the transmit channels 401, 403, 405, and 407 to the receive channels 411, 413, 415, and 417 of the capacitive sensor 315, in a state in which the at least one attribute is set as the first attribute may be a signal having a waveform of a square wave having a constant frequency.

A signal 433 transmitted from the transmit channels 401, 403, 405, and 407 to the receive channels 411, 413, 415, and 417 of the capacitive sensor 315 in the state in which the at least one attribute is set as the second attribute is illustrated in FIG. 4B.

A frequency of the signal 433 transmitted from the transmit channels 401, 403, 405, and 407 to the receive channels 411, 413, 415, and 417 of the capacitive sensor 315 in the state in which the at least one attribute is set as the second attribute may be different in a charging mode 441, and a hydrature measurement mode 443, respectively.

According to various embodiments of the present disclosure, the charging mode 441 may indicating a mode for charging the charge amount of the capacitive sensor 315 in order to measure the hydrature of the external object.

According to various embodiments of the present disclosure, the hydrature measurement mode 443 may indicate a mode of measuring the hydrature of the external object.

The frequency of the signal 433 in the charging mode 441 may be the same as the frequency of the signal 431 in the state in which the at least one attribute is set as the first attribute.

According to various embodiments of the present disclosure, the processor 320 may set the frequency of the signal 435 to be zero in the hydrature measurement mode 443. The fact that the frequency of the signal 435 is 0 may indicating that the charging of electrical charges in the capacitors 421 and 423 is blocked.

According to various embodiments of the present disclosure, when the signal input to the capacitive sensor 315 for charging is blocked, the charging of electric charge in the capacitive sensor 315 may stop. The processor 320 may block a signal input for charging the capacitive sensor 315 in order to confirm the change amount in electric charge of the capacitive sensor 315 occurring due to the contact of the external object.

According to various embodiments of the present disclosure, in order to accurately measure the hydrature of the external object, the processor 320 may stop the charging of electric charges in the capacitive sensor 315 in the hydrature measurement mode 443, and measure the hydrature of the external object based on the change amount or the magnitude in electric charges remaining in the capacitive sensor 315.

Figure 4C:
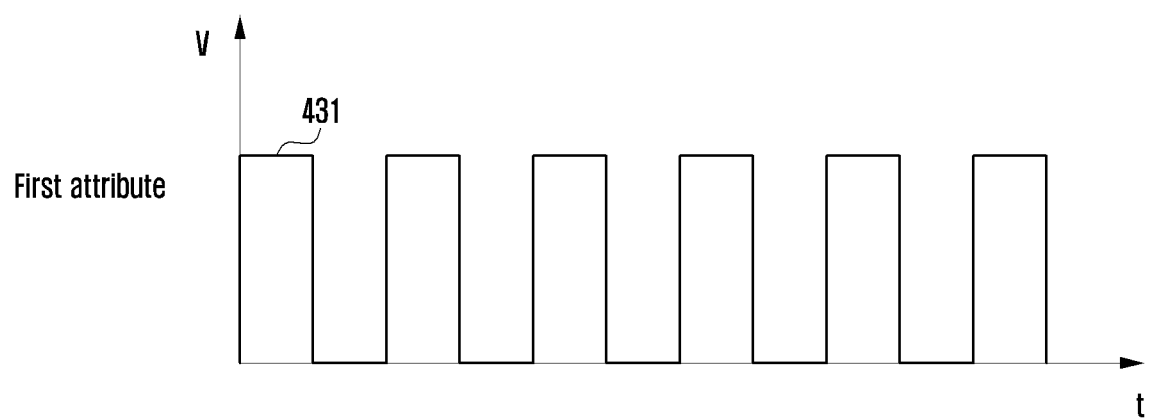
Figure 4C:
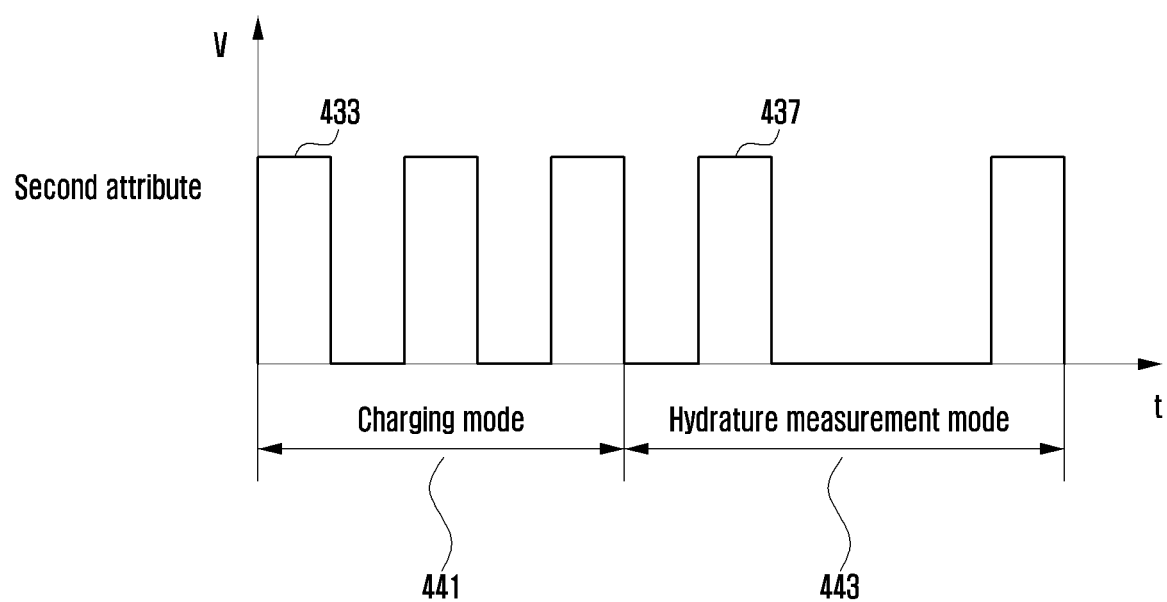

Referring to FIG. 4C, the frequency of the signal 433 transmitted from the transmit channels 401, 403, 405, and 407 to the receive channels 411, 413, 415, and 417 of the capacitive sensor 315 in the state in which the at least one attribute is set as the second attribute may be different in the charging mode 441 and the hydrature measurement mode 443, respectively.

According to various embodiments of the present disclosure, the processor 320 may set the frequency of the signal 437 in the hydrature measurement mode 443 to be lower than the frequency of the signal 431 in the state in which the at least one attribute is set as the first attribute. The fact that the frequency of the signal 437 is lowered may mean that the charging amount of electric charges in the capacitors 421 and 423 is reduced. The processor 320 may reduce a frequency of a signal input for charging the capacitive sensor 315 in order to accurately confirm the change amount in electric charge of the capacitive sensor 315 occurring due to the contact of the external object.

Figure 4D:
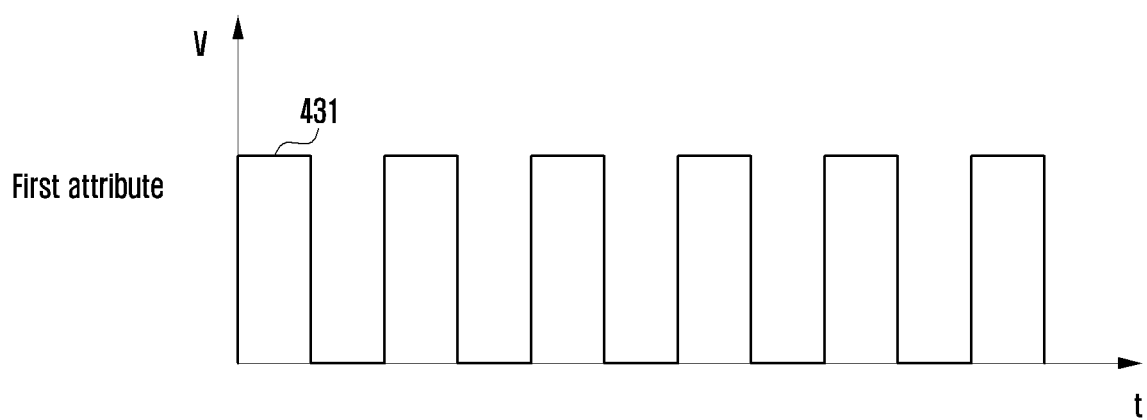
Figure 4D:
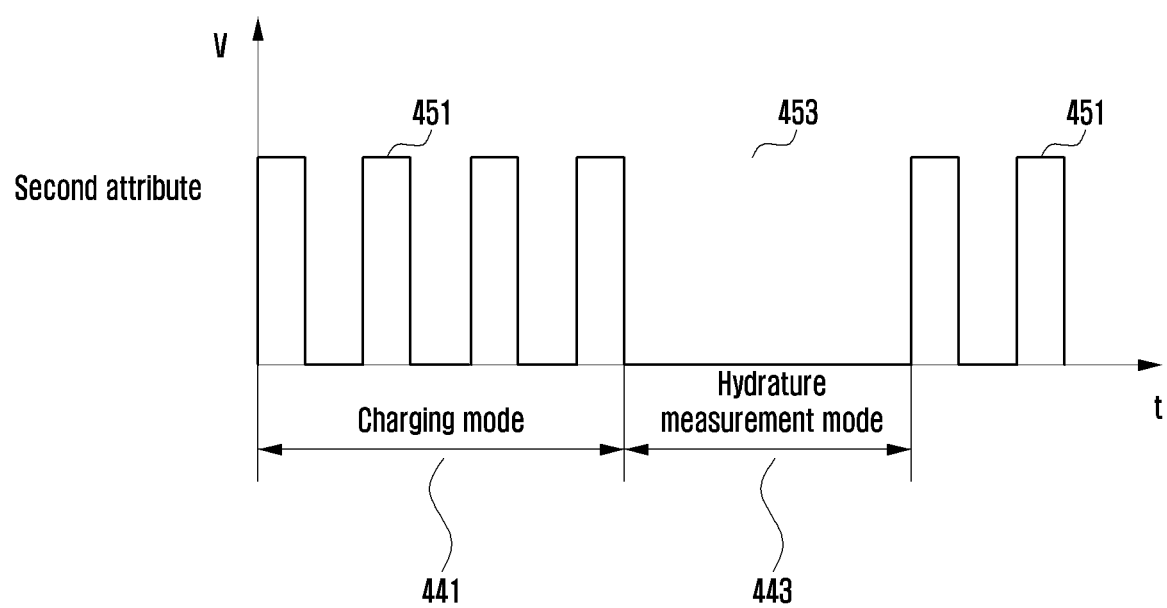
Figure 4E:
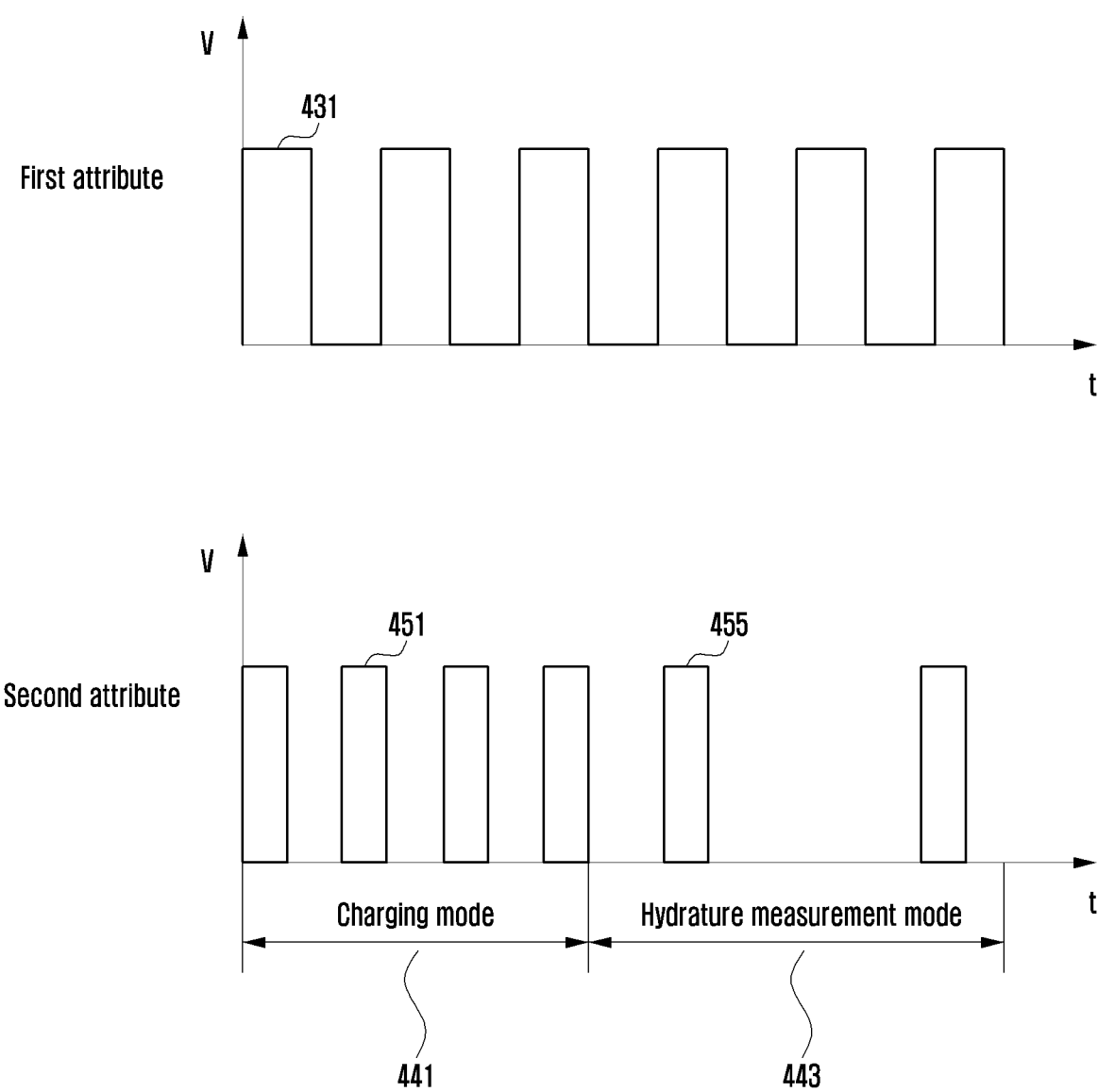

Referring to FIGS. 4D and 4E, the frequency of the signal 433 transmitted from the transmit channels 401, 403, 405, and 407 to the receive channels 411, 413, 415, and 417 of the capacitive sensor 315 in the state in which the at least one attribute is set as the second attribute may be different in the charging mode 441 and the hydrature measurement mode 443, respectively.

According to various embodiments of the present disclosure, the processor 320 may set the frequency of the signal 451 in the charging mode 441 to be higher than the frequency of the signal 431 in the state in which the at least one attribute is set as the first attribute. The reason of setting the frequency of the signal 451 to be high is to more charge the charge amount charged in the capacitors 421 and 423 in the charging mode 441 than the magnitude in charge amount charged in the capacitors 421 and 423 during the operation in the first attribute.

According to various embodiments of the present disclosure, the processor 320 may set the frequency of the signal 451 in the charging mode 441 to be higher than the frequency of the signal 431 in the state in which the at least one attribute is set as the first attribute so that the charge amount charged in the capacitors 421 and 423 becomes the maximum charge amount which can be stored in the capacitors 421 and 423.

The processor 320 may more charge electric charges in the capacitors 421 and 423 in the charging mode 441 to increase the resolution of the hydrature measurement of the external object.

According to various embodiments of the present disclosure, the processor 320 may vary the hydrature measurement mode to change the frequency of the signal 451 in the charging mode 441. For example, the processor 320 may increase the frequency of the signal 451 in the charging mode 441 and increase the resolution of the hydrature measurement, corresponding to the accurate hydrature measurement mode. As another example, the processor 320 may maintain the frequency of the signal 451 in the charging mode 441 to be equal to the frequency of the signal 431 in the state in which the at least one attribute is set as the first attribute, corresponding to the quick hydrature measurement mode.

Referring to FIG. 4D, the processor 320 may set the frequency of the signal 453 to be zero in the hydrature measurement mode 443. The fact that the frequency of the signal 453 is 0 may mean that the charging of electric charges in the capacitors 421 and 423 is blocked.

Referring to FIG. 4E, the processor 320 may set the frequency of the signal 455 in the hydrature measurement mode 443 to be lower than the frequency of the signal 431 in the state in which the at least one attribute is set as the first attribute. The fact that the frequency of the signal 455 is lowered may mean that the charging amount of electric charges in the capacitors 421 and 423 is reduced.

Figure 5:
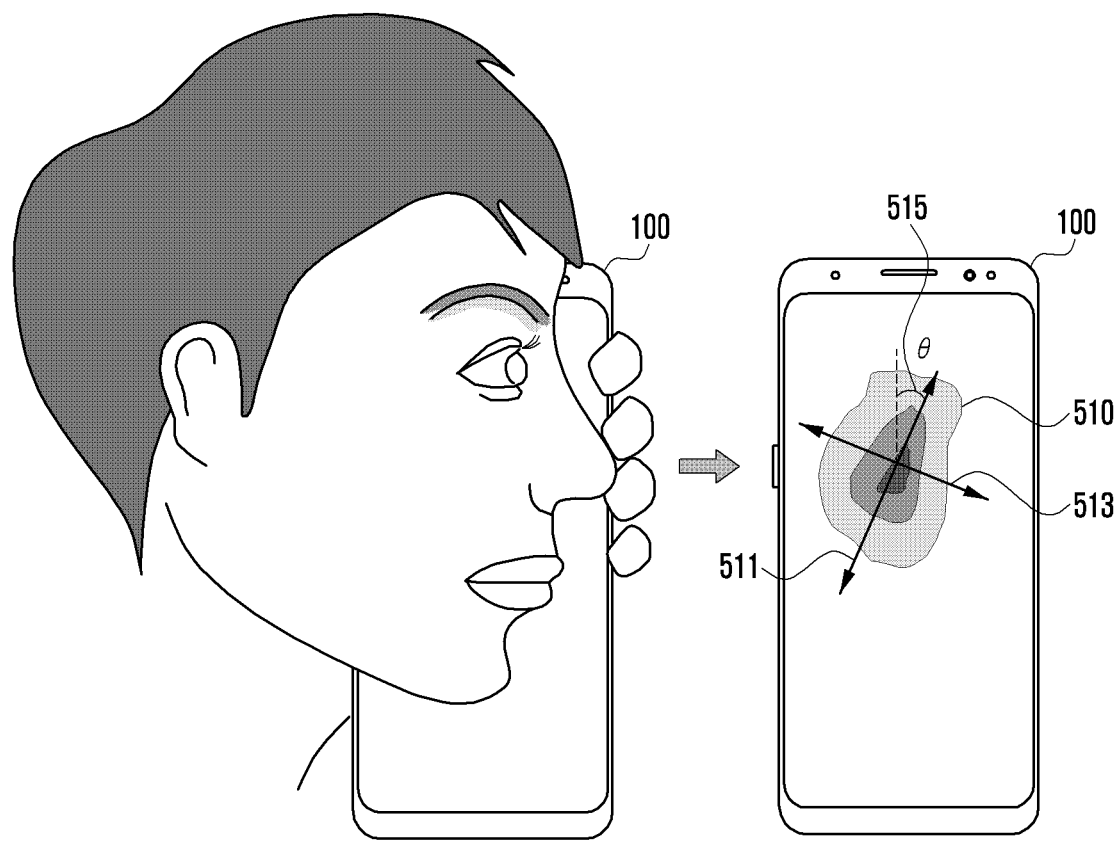
FIG. 5 is an illustration of a contact area of an external object with a display in the electronic device according to various embodiments of the present disclosure.

FIG. 5 is an illustration of a contact area of an external object with a display in the electronic device according to various embodiments of the present disclosure.

Referring to FIG. 5, the processor (e.g., the processor 320 in FIG. 3) of the electronic device (e.g., the electronic device 101 in FIG. 1) according to various embodiments of the present disclosure may set at least one attribute of a capacitive sensor (e.g., the capacitive sensor 315 in FIG. 3) as the second attribute when the specified condition is satisfied.

According to various embodiments of the present disclosure, the specified condition may mean various conditions which may be determined to measure the hydrature of the external object. The specified condition may include a condition that a size of a region in which an external object (e.g., a part of the user's face) contacts the display 310 is greater than or equal to a set value.

The processor 320 may confirm the size of the region in which the external object contacts the display 310 in order to confirm whether the specified condition is satisfied.

FIG. 5 illustrates an embodiment in which the processor 320 determines a size of a region 510 in which the external object (such as a portion of a user's face) contacts the display 310. Referring to FIG. 5, the processor 320 may determine the size of the region 510 based on a major axis 511 and a minor axis 513 of the region 510, and an angle 515 formed by the major axis 511, a vertical line, and the major axis 511.

In various embodiments of FIG. 5, the processor 320 may determine the size of the region 510.

Figure 6:
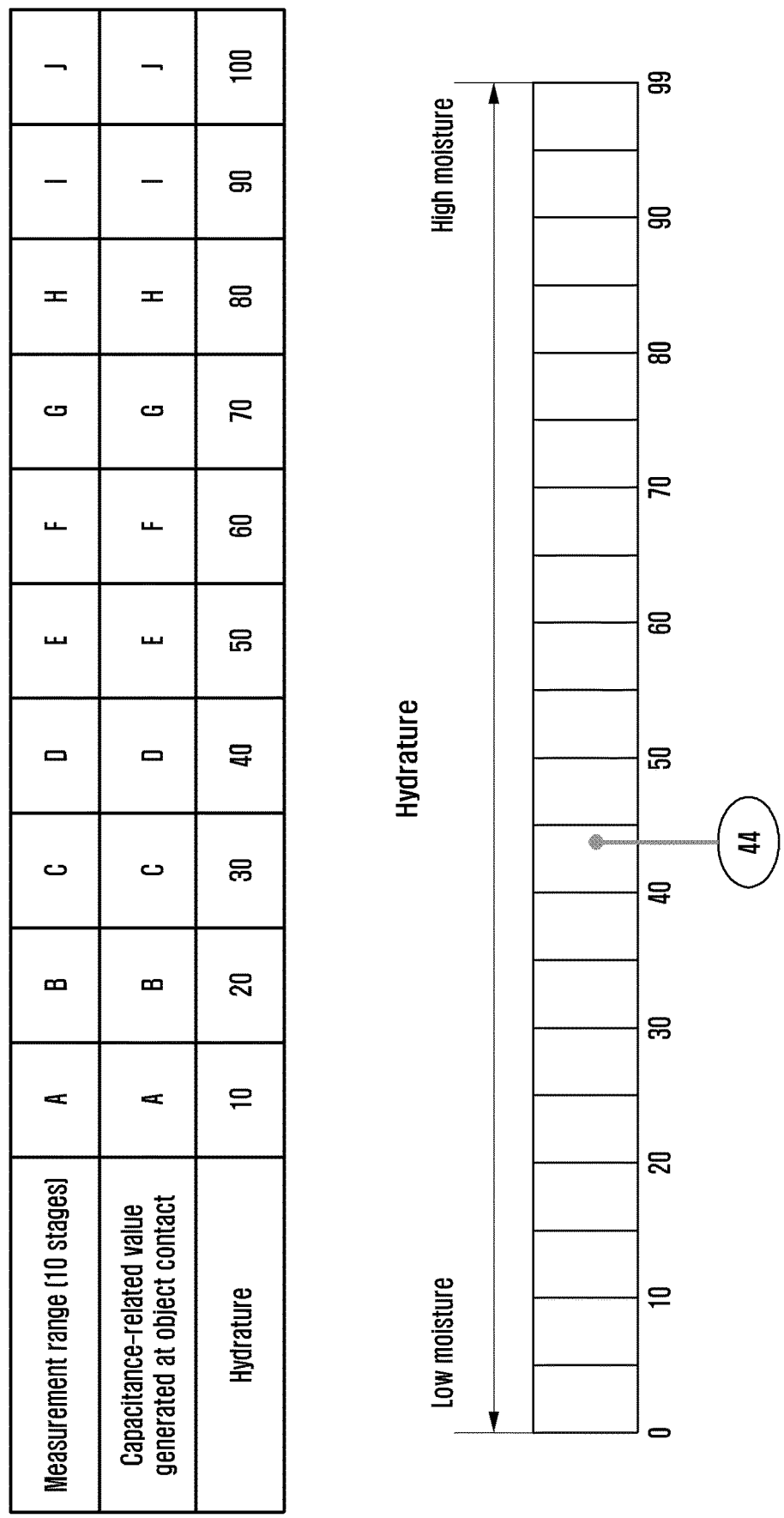
FIG. 6 is a diagram illustrating an example of a table in which a second data is mapped to hydrature, in the electronic device according to various embodiments of the present disclosure.

FIG. 6 is a diagram illustrating an example of a table in which a second data and hydrature are mapped, in the electronic device according to various embodiments of the present disclosure. As noted above, the second data may be associated with the change in the charge amount of the capacitive in the state in which the at least one attribute is set as the second attribute, effectively serving as a value related to capacitance that was generated at the moment the object contacts the display.

Referring to FIG. 6, it can be confirmed that a range of the second data and the hydrature mapped to the range of the second data are mapped.

The electronic device (e.g., the electronic device 101 in FIG. 1) according to various embodiments of the present disclosure may acquire the second data associated with the change in the charge amount of the capacitive sensor (e.g., the capacitive sensor 315 of FIG. 3) in the state in which the at least one attribute is set as the second attribute, and confirm the hydrature corresponding to the second data using a table illustrated in FIG. 6.

For example, the change in charge amount may vary depending on the hydrature of the external object. The higher the hydrature of the external object, the higher the electrical conductivity of the external object, and the more electric charge stored in the capacitors 421 and 423 will conduct and dissipate to the external object. Conversely, the lower the hydrature of the external object, the lower the electrical conductivity of the external object, and the less electric charge stored in the capacitors 421 and 423 will conduct and dissipate to the external object. Referring to the table illustrated in FIG. 6, it can be seen that the correlation between the hydrature of the external object and the second data is reflected.

According to various embodiments of the present disclosure, the differentiation of the measurement range of the second data may vary depending on the resolution at which the change amount in capacitance of the capacitive sensor 315 can be measured.

Referring to the table illustrated in FIG. 6, the measurement range of the second data may be differentiated into 10 stages. However, the present disclosure is not limited thereto, and may be differentiated into various stages (e.g., less or more) depending on the resolution at which the change amount of electric charges of the capacitive sensor 315 is to be measured.

The table illustrated in FIG. 6 shows that the change amount in electric charges and the hydrature are mapped, but may be implemented as the table in which the charge amount and the hydrature remaining in the capacitive sensor 315 rather than the change amount in electric charges are mapped.

According to various embodiments of the present disclosure, the electronic device 101 may provide an accurate hydrature measurement mode that increases accuracy upon the hydrature measurement and a quick hydrature measurement mode that supports quick hydrature measurement. Different tables can be used to differentiate the measurement range of the second data depending on the hydrature measurement mode (accurate hydrature measurement mode or quick hydrature measurement mode) in which the electronic device 101 operates.

Figure 7:
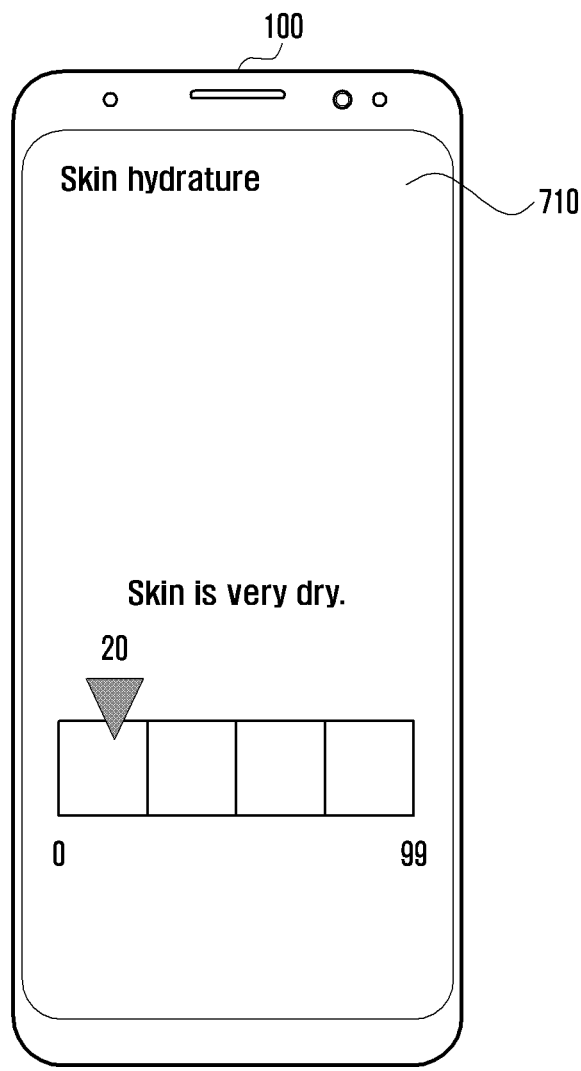
FIG. 7 is a diagram illustrating an example of displaying information associated with the measured hydrature, in the electronic device according to various embodiments of the present disclosure.

FIG. 7 is a diagram illustrating an example of displaying information associated with the measured hydrature, in the electronic device according to various embodiments of the present disclosure.

Referring to FIG. 7, the electronic device (e.g., the electronic device 101 in FIG. 1) according to various embodiments of the present disclosure displays information associated with the hydrature measured based on the second data on a display (e.g., the display 310 in FIG. 3, 710).

According to various embodiments of the present disclosure, the processor (e.g., the processor 320 in FIG. 3) may allow an application authorized to access data associated with the hydrature to use the measured hydrature. For example, the processor 320 may grant an access of an application providing hydrature information to the measured hydrature information. The processor 320 may output the measured hydrature and various additional information associated with the measured hydrature on the display 310.

Various information associated with the measured hydrature means various information such as a list of products associated with the measured hydrature, a result of a skin age of a user using the measured hydrature, information associated with an oil/water balance using the measured hydrature, proposal for water ingestion, etc.

According to various embodiments of the present disclosure, the processor 320 may further store history information associated with the measured hydrature in a memory (e.g., the memory 130 in FIG. 1), and display information associated with the history information on a display 710.

The electronic device according to various embodiments of the present disclosure includes a display including a capacitive sensor; and a processor, such that the processor is configured to set at least one attribute associated with the capacitive sensor as a first attribute, acquire a first data measured based on the capacitive sensor in response to a contact of an external object in a state in which the at least one attribute is set as the first attribute, determine a touch input to the display at least based on the first data, set the at least one attribute as a second attribute when a specified condition is satisfied, acquire a second data measured based on the capacitive sensor in response to the contact of the external object in a state in which the at least one attribute is set as the second attribute, and determine hydrature associated with the external object contacting the display at least based on the second data.

In the electronic device according to various embodiments of the present disclosure, the processor may be configured to change at least one of a charging rate or a discharging rate of the capacitive sensor based on at least a part of the operation of setting the at least one attribute as the second attribute.

In the electronic device according to various embodiments of the present disclosure, the processor may be configured to stop charging the capacitive sensor based on at least a part of the operation of setting the at least one attribute as the second attribute.

In the electronic device according to various embodiments of the present disclosure, the processor may be configured to change at least one of the charging rate or the discharging rate of the capacitive sensor to be further reduced than the charging rate or the discharging rate corresponding to the first attribute based on at least a part of the operation of setting the at least one attribute as the second attribute.

In the electronic device according to various embodiments of the present disclosure, the processor may be configured to increase the charging rate of the at least one capacitor in order to charge charging of at least one capacitor included in the capacitive sensor to be greater than or equal to the charge amount in the state in which the at least one attribute is set as the first attribute in response to determining that the specified condition is satisfied, and set the at least one attribute as the second attribute in response to confirming that the charge amount of the at least one capacitor is charged to be greater than or equal to the charge amount in the state in which the at least one attribute is set as the first attribute.

In the electronic device according to various embodiments of the present disclosure, the processor may be configured to set the charge amount charged in the capacitive sensor in the state in which the at least one attribute is set as the second attribute to be greater than the charge amount charged in the capacitive sensor in the state in which the at least one attribute is set as the first attribute based on at least a part of the operation of setting the at least one attribute as the second attribute.

In the electronic device according to various embodiments of the present disclosure, the processor may be configured to determine that the specified condition is satisfied when the electronic device enters a call mode.

In the electronic device according to various embodiments of the present disclosure, the processor may be configured to acquire status information associated with the electronic device via at least one of a proximity sensor, a grip sensor, or a communication module of the electronic device, and confirm whether the electronic device enters the call mode at least based on the status information.

In the electronic device according to various embodiments of the present disclosure, the processor may be configured to confirm information, which includes a contact area of the external object with the display and the time when the external object keeps contacting the display, based on the first data, and determine whether to satisfy the specified condition based on the confirmed information.

The electronic device according to various embodiments of the present disclosure further includes a memory in which the table in which the second data and the data associated with the hydrature are mapped is stored, such that the processor may be configured to determine the hydrature corresponding to the acquired second data based on the table.

Figure 8:
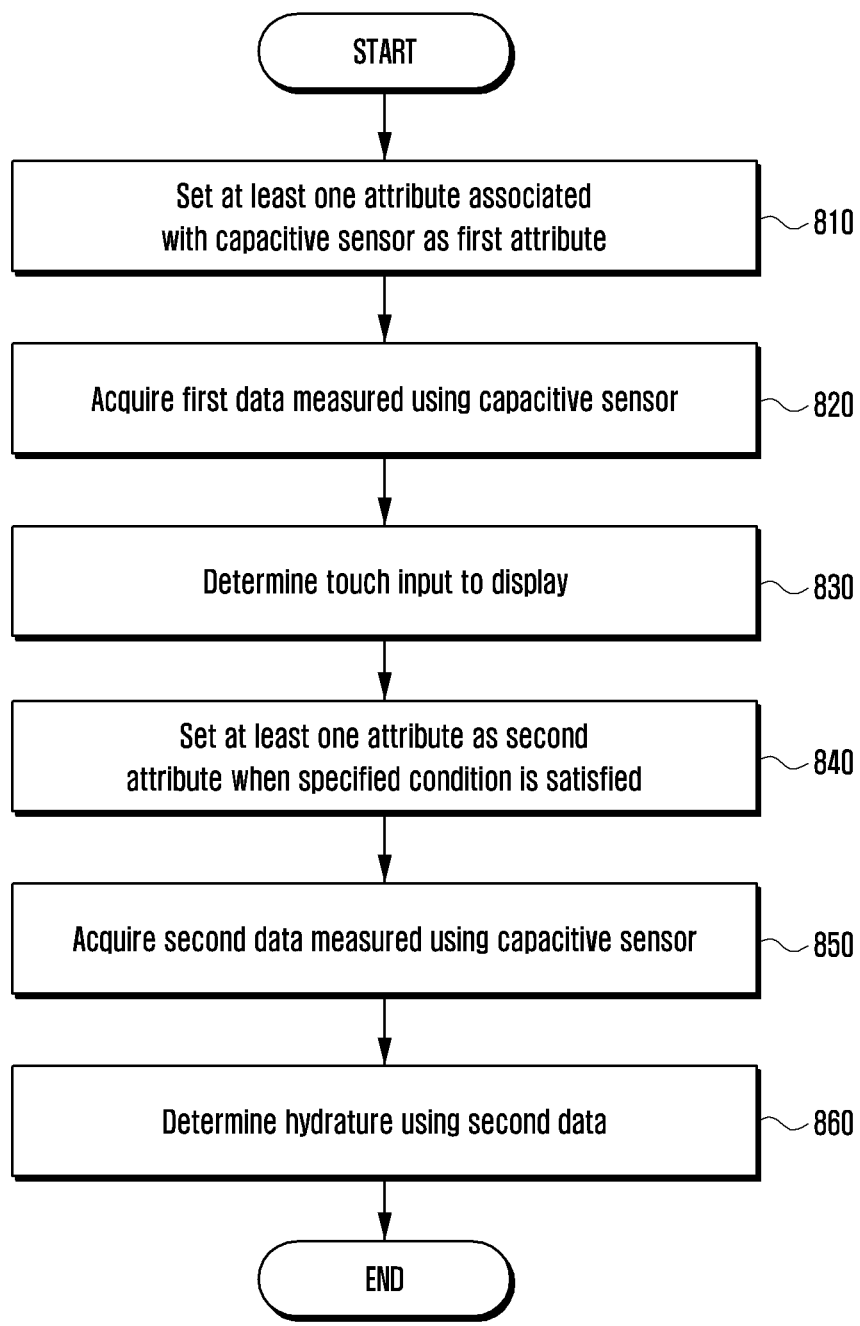
FIG. 8 is an operational flow chart of a method for operating an electronic device according to various embodiments of the present disclosure.

FIG. 8 is an operational flow chart of a method for operating an electronic device according to various embodiments of the present disclosure.

Referring to FIG. 8, at operation 810, the processor (e.g., the processor 320 in FIG. 3) may set at least one attribute associated with operation of the capacitive sensor (e.g., the capacitive sensor 315 in FIG. 3) using the first attribute.

According to various embodiments of the present disclosure, the first attribute may indicate a value for an variable associated with operation the capacitive sensor 315, for detecting a touch input on the display (e.g., the display 310 in FIG. 3) using the capacitive sensor 315.

At operation 820, the processor 320 may acquire first data associated with a change in capacitance in the display.

According to various embodiments of the present disclosure, the first data may be acquired when the capacitive sensor 315 is set as the first attribute, and indicate detection of a change in the charge amount measured by the capacitive sensor 315.

At operation 830, the processor 320 may determine that a touch input has occurred to the display 310, and the intended input corresponding to the touch input.

According to various embodiments of the present disclosure, the content displayed on the display 310 may refer to various screens and objects displayed thereon. For example, graphic objects such as a virtual keypad and a button selectable for performing a user input may be displayed on the display 310. According to various embodiments of the present disclosure, the processor 320 may "determine the touch" input, such as by interpreting the touch input to be a selection of a type of key input on the virtual keypad, a selection of a displayed button, etc. to the display 310, using on the first data corresponding to the determined touch input.

At operation 840, the processor 320 may set the attribute associated with operation the capacitive sensor 315 as the second attribute (e.g., a second value for operation of the sensor) if the specified condition is satisfied.

According to various embodiments of the present disclosure, the specified condition may include various conditions which may be determined to measure the hydrature of the external object. Various conditions such as a location and a size of a region in which the external object contacts the display 310, a pressure applied to the display 310 while the external object contacts the display 310, and a time when the external object keeps contacting the display 310 may refer to various conditions that can be determined to measure the hydrature of the external object. For example, if the area of the region in which the external object contacts the display 310 is greater than or equal to (or exceeds) a set value or the time when the external object keeps contacting the display 310 is greater than or equal to (or exceeds) the set value, the processor 320 may determine that the specified condition is satisfied.

According to various embodiments of the present disclosure, the processor 320 may determine whether the contact of the external object according to the guide information displayed on the display 310 satisfies the specified condition. According to various embodiments of the present disclosure, the guide information displayed on the display 310 may include guide information indicating a location at which an external object contacts the display 310, guide information indicating a time when an external object keeps contacting the display 310, guide information indicating a minimum contact area generated while the external object contacts the display 310, and the like.

According to various embodiments of the present disclosure, the processor 320 may change at least one attribute associated with the capacitive sensor 315 from the first attribute to the second attribute, in response to the determination that the specified condition is satisfied. The processor 320 may change the frequency of the signal input to the capacitive sensor 315 from a frequency corresponding to the first attribute to a frequency corresponding to the second attribute. By changing the frequency of the signal input to the capacitive sensor 315 to the frequency corresponding to the second attribute, the processor 320 may change a charge/discharge rate of the capacitive sensor 315.

At operation 850, the processor 320 may acquire the second data associated with the change in capacitance, meaning a second reading of a capacitance change based on a touch input, while the sensor is operator with the at least one attribute of the sensor is set to the second value (i.e., second attribute).

According to various embodiments of the present disclosure, the second data may include the actual change in capacitance, the changed amount (or "delta") of electric charges remaining in the capacitive sensor 315, the charge amount remaining in the capacitive sensor 315, and the like. The processor 320 can confirm the change amount in electric charges, the charge amount, and the like, and determine the hydrature of the external object based on the confirmed change amount in electric charges, charge amount or the like.

According to various embodiments of the present disclosure, the second data may be acquired in the state in which the capacitive sensor 315 is set as the second attribute.

At operation 860, the processor 320 may use the second data to determine the hydrature of the external object that contacts the display 310.

According to various embodiments of the present disclosure, the processor 320 may confirm the change amount in capacitance of the capacitive sensor 315 in the second data. The processor 320 may confirmed the hydrature mapped to the change amount confirmed in the table, which, as illustrated above, maps various hydrature values to a change value in capacitance charge.

Figure 9:
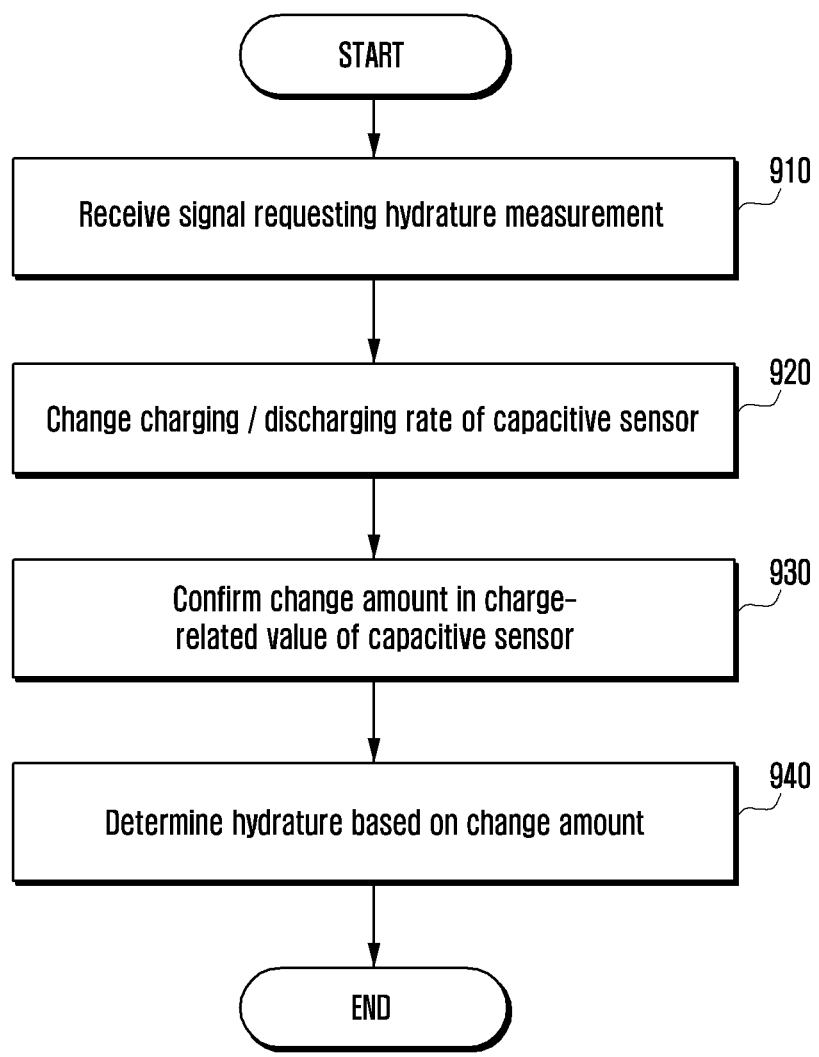
FIG. 9 is an operational flow chart of a method for operating an electronic device according to another embodiment of the present disclosure.

FIG. 9 is an operational flow chart of a method for operating an electronic device according to another embodiment of the present disclosure.

Referring to FIG. 9, at operation 910, the processor (e.g., the processor 320 in FIG. 3) may receive a signal requesting the hydrature measurement.

According to various embodiments of the present disclosure, the signal requesting the hydrature measurement may indicate a signal generated in an application which supports acquisition of the hydrature measurement. For example, the user of the electronic device (e.g., the electronic device 101 in FIG. 1) may execute this application, which may in turn generate the signal whether automatically or by the user's express input.

The processor 320 may receive the signal requesting the hydrature measurement, based events generated in the application that supports the hydrature measurement, such as a user input initiating a hydrature measurement.

At operation 920, the processor 320 may change the charging/discharging rate of the capacitive sensor (e.g., the capacitive sensor 315 in FIG. 3).

According to various embodiments of the present disclosure, the processor 320 may change the charge/discharge rate of the capacitive sensor 315 in response to the execution of the application that supports the hydrature measurement.

According to various embodiments of the present disclosure, the change in the charging/discharging rate of the capacitive sensor 315 may indicate that the capacitive sensor 315 is operated by being set in a configuration using or based on at the second attribute. The processor 320 may change the charging/discharging rate of the capacitive sensor 315 by changing the frequency of the signal transmitted from the transmit channel (e.g., the transmit channels 401, 403, 405, and 407 in FIG. 4A) of the capacitive sensor 315.

According to various embodiments of the present disclosure, the processor 320 may change the charging/discharging rate of the capacitive sensor 315 to allow the capacitive sensor 315 to set its charge amount based on or to be equal to a previously detected hydrature measurement value, which may be utilized as a maximum value.

According to various embodiments of the present disclosure, the processor 320 may change the frequency of the signal input to transmit channels 401, 403, 405, and 407 to zero, corresponding to the start of the hydrature measurement and block the charging of electric charge.

At operation 930, the processor 320 may confirm the change amount in the capacitance charge or charge amount of the capacitive sensor 315.

According to various embodiments of the present disclosure, the processor 320 may acquire the second data and use the second data to confirm the physical amount (capacitance, charge amount, etc.) of the capacitive sensor 315 or the change amount in the physical change of the capacitive sensor 315.

At operation 940, the processor 320 may determine the hydrature based on the change amount or the physical amount of the capacitive sensor 315.

According to various embodiments of the present disclosure, the processor 320 may confirm the change amount in capacitance of the capacitive sensor 315 as indicated in the second data. The processor 320 may then confirm the hydrature based on a hydrature value previously mapped to the detected change amount, as based on mapping indicated in a table (as described previously above).

Figure 10:
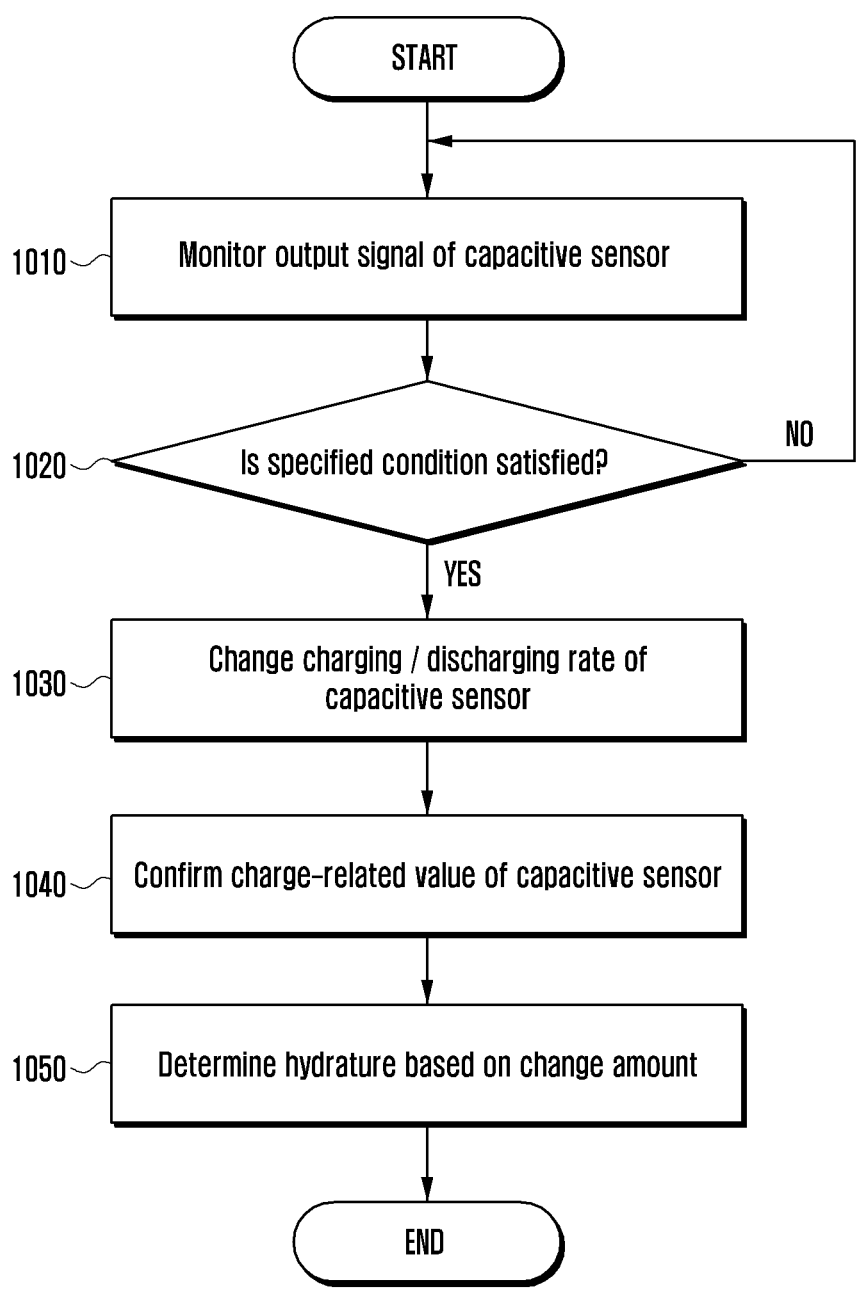
FIG. 10 is an operational flow chart of a method for operating an electronic device according to another embodiment of the present disclosure.

FIG. 10 is an operational flow chart of a method for operating an electronic device according to another embodiment of the present disclosure.

Referring to FIG. 10, at operation 1010, the processor (e.g., the processor 320 in FIG. 3) may monitor an output signal of the capacitive sensor (e.g., the capacitive sensor 315 in FIG. 3).

According to various embodiments of the present disclosure, the capacitive sensor 315 may output a signal while operating in a state in which at least one attribute associated with the capacitive sensor 315 is set as the first attribute.

The output signal from the capacitive sensor 315 may include information indicating that various external objects are contacting, near-contacting or otherwise approaching contact with the display (e.g., the display 310 in FIG. 3), and various information such as a location and an area of a region in which the external object contacts the display 310.

At operation 1020, the processor 320 may confirm that the specified condition is satisfied based on the output signal.

According to various embodiments of the present disclosure, the specified condition may include various conditions which may be determined to measure the hydrature of the external object. Various conditions such as a location and a size of a region in which the external object contacts the display 310, a pressure applied to the display 310 while the external object contacts the display 310, and a time when the external object keeps contacting the display 310 may refer to various conditions that can be determined to measure the hydrature of the external object. For example, if the area of the region in which the external object contacts the display 310 is greater than or equal to (or exceeds) a set value or the time when the external object keeps contacting the display 310 is greater than or equal to (or exceeds) the set value, the processor 320 may determine that the specified condition is satisfied.

According to various embodiments of the present disclosure, the processor 320 may perform the operations associated with the measurement of the hydrature when the physical amount (e.g., the size of the contact area, the contact holding time, etc.) generated by the contact of the external object satisfies the specified condition, regardless of the user intention of the electronic device 300. For example, when a portion (e.g., user's ear) of a user's body contacts or proximate the electronic device 300 (e.g., a situation in which the electronic device 300 performs a call), the processor 320 may set at least one attribute of the capacitive sensor 315 as the second attribute based on the first data including the size of the contact area generated while a part of the user's body contacts the display 310, the contact holding time, etc.

At operation 1030, the processor 320 may change the charging/discharging rate of the capacitive sensor 315.

According to various embodiments of the present disclosure, changing the charging/discharging rate of the capacitive sensor 315 may be an operation for measuring the hydrature.

At operation 1040, the processor 320 may confirm the change amount in the physical amount of the capacitive sensor 315.

According to various embodiments of the present disclosure, the change amount in the physical amount may vary depending on the hydrature value of the external object contacting the display 310.

At operation 1050, the processor 320 may determine the hydrature based on the change amount.

A method for operating an electronic device according to various embodiments of the present disclosure includes: an operation of setting at least one attribute associated with a capacitive sensor included in a display as a first attribute; an operation of acquiring a first data measured based on the capacitive sensor in response to a contact of an external object in a state in which the at least one attribute is set as the first attribute; an operation of determining a touch input to the display at least based on the first data; and an operation of setting the at least one attribute as a second attribute when a specified condition is satisfied; an operation of acquiring a second data measured based on the capacitive sensor in response to the contact of the external object in a state in which the at least one attribute is set as the second attribute; and an operation of determining hydrature associated with the external object contacting the display at least based on the second data.

In the method for operating an electronic device according to various embodiments of the present disclosure, the operation of setting the at least one attribute as the second attribute may include an operation of changing at least one of a charging rate or a discharging rate of the capacitive sensor.

In the method for operating an electronic device according to various embodiments of the present disclosure, the operation of setting the at least one attribute as the second attribute may include an operation of stopping charging the capacitive sensor.

In the method for operating an electronic device according to various embodiments of the present disclosure, the operation of setting the at least one attribute as the second attribute may include an operation of further reducing at least one of the charging rate or the discharging rate of the capacitive sensor than the charging rate or the discharging rate corresponding to the first attribute.

In the method for operating an electronic device according to various embodiments of the present disclosure, the operation of setting the at least one attribute as the second attribute may include: an operation of increasing the charging rate of the at least one capacitor in order to charge charging of at least one capacitor included in the capacitive sensor to be greater than or equal to the charge amount in the state in which the at least one attribute is set as the first attribute in response to determining that the specified condition is satisfied, and an operation of setting the at least one attribute as the second attribute in response to confirming that the charge amount of the at least one capacitor is charged to be greater than or equal to the charge amount in the state in which the at least one attribute is set as the first attribute.

In the method for operating an electronic device according to various embodiments of the present disclosure, the operation of setting the at least one attribute as the second attribute may include an operation of setting the capacitive sensor so that the charge amount charged in the capacitive sensor in the state in which the at least one attribute is set as the second attribute is greater than the charge amount charged in the capacitive sensor in the state in which the at least one attribute is set as the first attribute.

The method for operating an electronic device according to various embodiments of the present disclosure may further include: an operation of confirming whether the electronic device enters a call mode; and an operation of determining that the specified condition is satisfied when the electronic device enters the call mode.

In the method for operating an electronic device according to various embodiments of the present disclosure, the operation of confirming whether the electronic device enters the call mode may include: an operation of acquiring status information associated with the electronic device via at least one of a proximity sensor, a grip sensor, or a communication module of the electronic device; and an operation of confirming whether the electronic device enters the call mode at least based on the status information.

The method for operating an electronic device according to various embodiments of the present disclosure may further include: an operation of confirming information, which includes a contact area of the external object with the display and time when the external object keeps contacting the display, based on the first data; and an operation of determining whether to satisfy the specified condition based on the confirmed information.

In the method for operating an electronic device according to various embodiments of the present disclosure, the operation of determining the hydrature may include an operation of determining the hydrature corresponding to the second data using a table in which the second data stored in a memory of the electronic device and data associated with the hydrature are mapped.

The above-discussed method is described herein with reference to flowchart illustrations, methods, and computer program products according to example embodiments of the present disclosure. It will be understood that each block of the flowchart illustrations, and combinations of blocks in the flowchart illustrations, can be implemented by computer program instructions. These computer program instructions can be provided to a processor of a general purpose computer, special purpose computer, or other programmable data processing apparatus to produce a machine, such that the instructions, which are executed via the processor of the computer or other programmable data processing apparatus, create means for implementing the functions specified in the flowchart block or blocks. These computer program instructions may also be stored in a computer usable or computer-readable memory that can direct a computer or other programmable data processing apparatus to function in a particular manner, such that the instructions stored in the computer usable or computer-readable memory produce an article of manufacture including instruction means that implement the function specified in the flowchart block or blocks. The computer program instructions may also be loaded onto a computer or other programmable data processing apparatus to cause a series of operations to be performed on the computer or other programmable apparatus to produce a computer implemented process such that the instructions that are executed on the computer or other programmable apparatus provide operations for implementing the functions specified in the flowchart block or blocks.

And each block of the flowchart illustrations may represent a module, segment, or portion of code, which includes one or more executable instructions for implementing the specified logical function(s). It should also be noted that in some alternative implementations, the functions noted in the blocks may occur out of the order. For example, two blocks shown in succession may in fact be executed substantially concurrently or the blocks may sometimes be executed in the reverse order, depending upon the functionality involved.

Certain example aspects of the present disclosure can also be embodied as computer readable code on a non-transitory computer readable recording medium. A non-transitory computer readable recording medium is any data storage device that can store data which can be thereafter read by a computer system. Examples of the non-transitory computer readable recording medium include a ROM, a RAM, compact disc-ROMs (CD-ROMs), magnetic tapes, floppy disks, and optical data storage devices. The non-transitory computer readable recording medium can also be distributed over network coupled computer systems so that the computer readable code is stored and executed in a distributed fashion. In addition, functional programs, code, and code segments for accomplishing the present disclosure can be easily construed by programmers skilled in the art to which the present disclosure pertains.

At this point it should be noted that the various example embodiments of the present disclosure as described above typically involve the processing of input data and the generation of output data to some extent. This input data processing and output data generation may be implemented in hardware or software in combination with hardware. For example, specific electronic components may be employed in a mobile device or similar or related circuitry for implementing the functions associated with the various example embodiments of the present disclosure as described above. Alternatively, one or more processors operating in accordance with stored instructions may implement the functions associated with the various embodiments of the present disclosure as described above. If such is the case, it is within the present disclosure that such instructions may be stored on one or more non-transitory processor readable mediums. Examples of the processor readable mediums include a ROM, a RAM, CD-ROMs, magnetic tapes, floppy disks, and optical data storage devices. The processor readable mediums can also be distributed over network coupled computer systems so that the instructions are stored and executed in a distributed fashion. In addition, functional computer programs, instructions, and instruction segments for accomplishing the present disclosure can be easily construed by programmers skilled in the art to which the present disclosure pertains.

Aspects of the above-described embodiments of the present disclosure can be implemented in hardware, firmware or via the execution of software or computer code that can be stored in a recording medium such as a CD ROM, a Digital Versatile Disc (DVD), a magnetic tape, a RAM, a floppy disk, a hard disk, or a magneto-optical disk or computer code downloaded over a network originally stored on a remote recording medium or a non-transitory machine readable medium and to be stored on a local recording medium, so that the methods described herein can be rendered via such software that is stored on the recording medium using a general purpose computer, or a special processor or in programmable or dedicated hardware, such as an ASIC or FPGA. As would be understood in the art, the computer, the processor, microprocessor controller or the programmable hardware include memory components, e.g., RAM, ROM, Flash, etc. that may store or receive software or computer code that when accessed and executed by the computer, processor or hardware implement the processing methods described herein.

While the present disclosure has been illustrated and described with reference to various example embodiments thereof, it will be understood by those skilled in the art that various changes in form and details may be made therein without departing from the present disclosure as defined by the appended claims and their equivalents.

What is claimed is:

1. An electronic device, comprising:
a display including a capacitive sensor; and
at least one processor configured to:
set at least one operational attribute of the capacitive sensor using a first value,
acquire a first data measurement from the capacitive sensor when an external object contacts the display while the at least one attribute is set using the first value and determine that a touch input has occurred based on the first data,
when the touch input satisfies a prespecified condition:
reduce a frequency of a signal input to the capacitive sensor to change at least one of a charging rate or a discharging rate of the capacitive sensor,
acquire a second data measurement from the capacitive sensor while the external object contacts the display when the at least one operational attribute is set using the second value, and
determine a hydration value associated with the external object at least based on the acquired second data measurement, and
when the touch input does not satisfy the prespecified condition, maintain the frequency.

2. The electronic device of claim 1, wherein setting the at least one operational attribute using the second value includes terminating charging of the capacitive sensor.

3. The electronic device of claim 1, wherein when the at least one operational attribute is set using the second value, a charging or discharging rate of the capacitive sensor is less than when the operational attribute is set using the first value.

4. The electronic device of claim 1, wherein the at least one processor is further configured to:
in response to determining the prespecified condition is satisfied, increase a charging rate of at least one capacitor in the capacitive sensor to charge the at least one capacitor included in the capacitive sensor when the at least one attribute is set using the first value, and
set the at least one attribute using the second value in response to confirming that a charge amount of the at least one capacitor is charged to be greater than or equal to a previous charge amount via an increased charging rate.

5. The electronic device of claim 1, wherein when the at least one operational attribute is set using the second value, a charging or discharging rate of the capacitive sensor is greater than when the operational attribute is set using the first value.

6. The electronic device of claim 1, further comprising:
a microphone,
a speaker, and communication circuitry,
wherein the prespecified condition is satisfied when the electronic device is in a call mode.

7. The electronic device of claim 6, further including at least one of a proximity sensor, a grip sensor, and a communication module, the at least one processor further configured to:
detect whether the electronic device is in the call mode using at least one of the proximity sensor, the grip sensor and the communication module.

8. The electronic device of claim 1, wherein the at least one processor is further configured to:
detect, based on the first data, at least a contact area of the external object with the display and a time through which the external object maintains contact with the display,
wherein satisfaction of the prespecified condition further includes detecting that the detected time is greater than or equal to a prespecified time or the detected contact area being greater than or equal to a prespecified area.

9. The electronic device of claim 1, further comprising:
a memory storing a table in which potential values for the second data measurements are respectively mapped to a range of hydration values,
wherein the hydration value associated with the external object is determined based on the acquired second data measurement and mapping indicated in the stored table.

10. A method in an electronic device, comprising:
setting at least one operational attribute of a capacitive sensor using a first value,
acquiring, by at least one processor, a first data measurement from the capacitive sensor in when an external object contacts a display while the at least one attribute is set using the first value and determine that a touch input has occurred based on the first data,
when the touch input satisfies a prespecified condition:
reduce a frequency of a signal input to the capacitive sensor to change at least one of a charging rate or a discharging rate of the capacitive sensor,
acquiring a second data measurement from the capacitive sensor while the external object contacts the display, when the at least one operational attribute is set using the second value, and
determining a hydration value associated with the external object at least based on the acquired second data measurement, and
when the touch input does not satisfy the prespecified condition, maintain the frequency.

11. The method of claim 10, wherein setting the at least one operational attribute using the second value includes terminating charging of the capacitive sensor.

12. The method of claim 10, wherein when the at least one operational attribute is set using the second value, a charging or discharging rate of the capacitive sensor is less than when the operational attribute is set using the first value.

13. The method of claim 10, wherein the at least one processor is further configured to:
increase a charging rate of at least one capacitor in the capacitive sensor to set charging of the at least one capacitor greater than or equal to a charge amount of the capacitive sensor when the at least one attribute is set using the first value, and
wherein the at least one attribute is set using the second value in response to confirming that the charge amount of the at least one capacitor is greater than or equal to a previous charge amount when the at least one attribute was set as the first value.

14. The method of claim 10, wherein when the at least one operational attribute is set using the second value, a charging or discharging rate of the capacitive sensor is greater than when the operational attribute is set using the first value.

15. The method of claim 10, wherein the prespecified condition is satisfied when the electronic device is in a call mode.

16. The method of claim 15, further including at least one of a proximity sensor, a grip sensor, and a communication module, the at least one processor further configured to:
detect whether the electronic device is in the call mode using at least one of the proximity sensor, the grip sensor and the communication module.

17. The method of claim 10, wherein the at least one processor is further configured to:
detect, based on the first data, at least a contact area of the external object with the display and a time through which the external object maintains contact with the display,
wherein satisfaction of the prespecified condition further includes detecting that the detected time is greater than or equal to a prespecified time.

18. The method of claim 10, wherein the electronic device includes a memory storing a table in which potential values for the second data measurements are respectively mapped to a range of hydration values, and
wherein the hydration value associated with the external object is determined based on the acquired second data measurement and mapping indicated in the stored table.

19. An electronic device, comprising:
a display including a capacitive sensor; and
at least one processor configured to:
set at least one operational attribute of the capacitive sensor using a first value,
when a touch input is received and the touch input has an area greater than a predetermined area:
reduce a frequency of a signal input to the capacitive sensor to change at least one of a charging rate or a discharging rate of the capacitive sensor,
acquire a first data measurement from the capacitive sensor while an external object contacts the display when the at least one operational attribute is set using a first value, and
determine a hydration value associated with the external object at least based on the acquired first data measurement,
when the touch input is not received or when the area of the touch input is less than the predetermined area, maintain the frequency.

* * * * *